(12) United States Patent
Chen et al.

(10) Patent No.: US 6,299,869 B1
(45) Date of Patent: **\*Oct. 9, 2001**

(54) HUMAN INTERFERON-EPSILON: A TYPE I INTERFERON

(75) Inventors: Jian Chen, San Mateo; Paul Godowski, Burlingame; William I. Wood, Hillsborough; Dong-Xiao Zhang, Burlingame, all of CA (US)

(73) Assignee: Genentech, Inc., So. San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/202,122

(22) PCT Filed: Dec. 3, 1998

(86) PCT No.: PCT/US98/25672

§ 371 Date: Mar. 4, 1999

§ 102(e) Date: Mar. 4, 1999

(87) PCT Pub. No.: WO99/29863

PCT Pub. Date: Jun. 17, 1999

Related U.S. Application Data

(60) Provisional application No. 60/106,463, filed on Oct. 30, 1998, provisional application No. 60/084,045, filed on May 4, 1998, and provisional application No. 60/067,897, filed on Dec. 8, 1997.

(51) Int. Cl.$^7$ .......................... A61K 38/21; A61K 38/00; C07K 14/00; C07H 21/04; C12P 21/04

(52) U.S. Cl. ................... 424/85.4; 530/351; 530/350; 536/23.1; 536/23.52; 514/2; 514/12; 435/69.51; 435/23.5; 435/320.1; 435/325; 435/252.33; 435/259.2; 435/358; 435/69.1; 435/69.2

(58) Field of Search .................................. 530/351, 350; 435/69.51, 23.5, 320.1, 323, 252.33, 259.2, 358, 69.1, 69.2; 424/85.7, 85.4; 536/23.1, 23.52; 514/2, 12

(56) References Cited

U.S. PATENT DOCUMENTS 4,423,147  12/1983  Secher et al. .

FOREIGN PATENT DOCUMENTS

| 307247 | 3/1989 | (EP) . |
| 032134 B2 | 10/1993 | (EP) . |
| 2079291 | 1/1982 | (GB) . |
| 2123835 | 2/1984 | (GB) . |
| 2161270 | 1/1986 | (GB) . |
| 2161487 | 1/1986 | (GB) . |
| WO 93/04699 | 3/1993 | (WO) . |

OTHER PUBLICATIONS

Adams et al., "Use of a random human BAC end sequence database for sequence–ready map building" (EMBL Database Entry Accession No. AQ111637) (Sep. 4, 1998).

Alkan and Braun, "Epitope mapping of human recombinant interferon alpha molecules by monoclonal antibodies" *Synthetic peptides as antigens—Ciba Foundation Symposium 119* 119:264–278 (1986).

Barasoain et al., "Antibodies against a peptide representative of a conserved region of human IFN–α. Differential effects on the antiviral and antiproliferative effects of IFN" *Journal of Immunology* 143(2):507–512 (Jul. 15, 1989).

Baron et al., "From cloning to a commercial realization: human alpha interferon" *Crit. Rev. Biotech.* 10(3):179–190 (1990).

Bolivar et al., "Construction and Characterization of New Cloning Vehicles. II. A Multipurpose Cloning System" *Gene* 2:95–113 (1977).

Capon et al., "Designing CD4 Immunoadhesins for AIDS Therapy" *Nature* 337:525–531 (Feb. 9, 1989).

Capon et al., "Two distinct families of human and bovine interferon–α genes are coordinately expressed and encode functional polypeptides" *Molecular & Cellular Biology* 5:768–779 (1985).

Dafny et al., "Interferon modulates neuronal activity recorded from the hypothalamus, thalamus, hippocampus, amygdala and the somatosensory cortex" *Brain Research* 734(1–2):269–274 (Sep. 23, 1996).

Darnell, Jr. et al., "Jak–STAT Pathways and Transcriptional Activation in Response to IFNs and Other Extracellular Signaling Proteins" *Science* 264(5164):1415–1421 (Jun. 3, 1994).

De Boer et al., "Construction of a tandem trp–lac promoter and a hybrid trp–lac promoter for efficient and controlled expression of the human growth hormone gene in *Escherichia coli*" *Promoter Structure and Function*, Rodriguez et al., New York:Praeger Publishers, Chapter 29, pp. 462–481 (1982).

De Maeyer and De Maeyer–Guignard, "Interferons" *The Cytokine Handbook*, 2nd edition, Chapter 15, pp. 265–288 (1994).

De Maeyer, E., "The Presence and Possible Pathogenic Role of Interferons in Disease" *Interferons and other Regulatory Cytokines*, John Wiley and Sons Publishers, Chapter 16, pp. 380–424 (1988).

Duarte et al., "Anticuerpos monoclonales de raton contra el interferon recombinante alfa 2. Su empleo en la purificacion y deteccion del antigeno" *Interferon y Biotechnologia* (An English language summary appears on the front page of the article) 4(3) :221–232 (1987).

Evinger and Pestka, "Assay of growth inhibition in lymphoblastoid cell cultures" *Methods in Enzymology* 79(Pt B) : 362–368 (1981).

(List continued on next page.)

*Primary Examiner*—Elizabeth Kemmerer
*Assistant Examiner*—Janet L. Andres
(74) *Attorney, Agent, or Firm*—Atulya R. Agarwal

(57) ABSTRACT

The invention concerns a human interferon-ϵ, originally designated PRO655, and its variants and derivatives. The interferon is related to but distinct from members of the IFN-α family and from IFNs-β and -γ. Nucleic acid encoding the polpypeptide, and methods and means for their recombinant production are also included.

25 Claims, 12 Drawing Sheets

OTHER PUBLICATIONS

Exley et al., "A comparison of the neutralizing properties of monoclonal and polyclonal antibodies to human interferon alpha" *Journal of General Virology* 65:2277–2280 (1984).

Farkkila et al., "Clinical spectrum of neurological herpes simplex infection" *Acta Neurologica Scandinavica* 87(4) : 325–328 (1993).

Feng et al., "Progressive Alignment and Phylogenetic Tree Construction of Protein Sequences" *Methods in Enzymology* 183:375–387 (1990).

Gibbs et al., "A negative regulatory region in the intracellular domain of the human interferon–α receptor" *Journal of Biological Chemistry* 271(45):28710–28716 (Nov. 8, 1996).

Goeddel et al., "Human Leukocyte Interferon Produced by *E. coli* Is Biologically Active" *Nature* 287(5781):411–416 (Oct. 2, 1980).

Goeddel et al., "Synthesis of Human Fibroblast Interferon by *E. coli*" *Nucleic Acids Research* 8(18):4057–4074 (1980).

Goeddel et al., "The structure of eight distinct cloned human leukocyte interferon cDNAs" *Nature* 290:20–26 (1981).

Gray et al., "Expression of Human Immune Interferon cDNA in *E. coli* and Monkey Cells" *Nature* 295:503–508 (Feb. 11, 1982).

Heidemann et al., "Gunstigerer verlauf des herpes zoster bei immunsupprimierten patienten unter behandlung mit fibroblasteninterferon" *Onkologie* (An English language summary appears on the front page of the article) 7:210–212 (1984).

Hertzog et al., "Neutralization of interferon α4 by a monoclonal antibody which blocks signal transduction" *Journal of Interferon Research* (abstract #119–15) 10(Suppl. 1):5170 (1990).

Holmes et al., "Structure and Functional Expression of a Human Interleukin–8 Receptor" *Science* 253(5025):1278–1280 (Sep. 13, 1991).

Knobler et al., "Systemic alpha–interferon therapy of multiple sclerosis" *Neurology* 34:1273–1279 (Oct. 1984).

Knoll and Lichter, "In situ hybridization and detection using nonisotopic probes" *Current Protocols in Molecular Biology* (Unit 14.7.1–14.7.14), Ausubel et al., New York:John Wiley & Sons (1995).

Knoll and Lichter, "In situ hybridization to metaphase chromosomes and interphase nuclei" *Current Protocols in Human Genetics* (Units 4.3.1–4.3.28), Dracopoli et al., New York:John Wiley & Sons vol. 1 (1995).

Konstek et al., "Distinct effect of pH 2 on a common antigenic structure found in human interferons–$\alpha_1$ and –$\alpha_2$ in the region 30–35" *Journal of Interferon Research* 11:327–332 (1991).

"Labeling and colorimetric detection of nonisotopic probes" *Current Protocols in Molecular Biology* (Unit 3.18), Ausubel et al., New York:John Wiley & Sons pp. 3–42—3–46 (1997).

Lawn et al., "DNA sequence of two closely linked human leukocyte interferon genes" *Science* 212(4499):1159–1162 (Jun. 5, 1981).

Levy et al., "Cytoplasmic Activation of ISGF3, the Positive Regulator of Interferon–α–Stimulated Transcription, Reconstructed In Vitro" *Genes & Development* 3:1362–1371 (1989).

Lu et al., "Structure–function study of the extracellular domain of the human IFN–α receptor (hIFNAR1) using blocking monoclonal antibodies: the role of domains 1 and 2" *Journal of Immunology* 160(4):1782–1788 (Feb. 15, 1998).

Lund et al., "Novel cluster of α–interferon gene sequences in a placental cosmid DNA library" *Proc. Natl. Acad. Sci. USA* 81(8):2435–2439 (Apr. 1984).

Merigan et al., "Human leukocyte interferon for the treatment of herpes zoster in patients with cancer" *N. Engl. J. Med* 298(18):981–987 (May 4, 1978).

Morehead et al., "Roles of the 29–138 disulfide bond of subtype A of human α interferon in its antiviral activity and conformational stability" *Biochemistry* 23(11):2500–2507 (May 22, 1984).

Nagata et al., "Synthesis in *E. coli* of a polypeptide with human leukocyte interferon activity" *Nature* 284(5754) : 316–320 (1980).

Nagata et al., "The structure of one of the eight or more distinct chromosomal genes for human interferon–α" *Nature* 287(5781):401–408 (Oct. 2, 1980).

Noll et al., "Production and characterization of four monoclonal antibodies specific for human interferon–alpha–1 and –alpha–2" *Biomedica Biochimica Acta* 48(1):165–176 (1989).

Novick et al., "The human interferon α/β receptor: characterization and molecular cloning" *Cell* 77:391–400 (1994).

Pestka, S., "The human interferon–α species and hybrid proteins" *Seminars in Oncology* 24(3 Supp.9):S9–4—S9–17 (Jun. 1997).

Pestka, S., "The human interferons—from protein purification and sequence to cloning and expression in bacteria: before, between, and beyond" *Archives of Biochemistry & Biophysics* 221(1):1–37 (Feb. 15, 1983).

Pfeffer, L., "Biologic activities of natural and synthetic type I interferons" *Seminars in Oncology* 24(3 Suppl 9):S9–63—S9–69 (Jun. 1997).

Picken et al., "Nucleotide sequence of the gene for heat–stable enterotoxin II of *Escherichia coli*" *Infection and Immunity* 42(1):269–275 (1983).

Plioplys and Massimini, "Alpha/beta interferon is a neuronal growth factor" *Neuroimmunomodulation* 2(1):31–35 (Jan.–Feb. 1995).

Reis et al., "Antigenic characterization of human interferon derived from amniotic membranes induced by virus" *Journal of Interferon Research* 9(5):573–581 (Oct. 1989).

Rubinstein et al., "Convenient assay for interferons" *Journal of Virology* 37(2) :755–758 (Feb. 1981).

Ruppert et al., "Cloning and Expression of Human $TAF_{II}250$: a TBP–associated Factor Implicated in Cell–cycle Regulation" *Nature* 362:175–179 (1993).

Scholtissek et al., "A cloning cartridge of λ $t_o$ terminator" *Nucl. Acids Res.* 15(7) :3185 (1987).

Shearer et al., "Monoclonal antibodies that distinguish between subspecies of human interferon–α and that detect interferon oligomers" *Journal of Immunology* 133(6) : 3096–3101 (Dec. 1984).

Sompayrac et al., "Efficient infection of monkey cells with DNA of simian virus 40" *Proc. Natl. Acad. Sci. USA* 78(12):7575–7578 (Dec. 1981).

Stancek et al., "Interferon–neutralizing or enhancing activities in hybridoma cell fluids after in vitro immunization" *Acta Virologica* 36(4):376–382 (Aug. 1992).

Streuli et al., "At least three human type α interferons: structure of α2" *Science* 209(4463):1343–1347 (Sep. 19, 1980).

Taniguchi et al., "Human leukocyte and fibroblast interferons are structurally related" *Nature* 285:547–549 (1980).

Thimmappaya et al., "Adenovirus VAI RNA is required for efficient translation of viral mRNAs at late times after infection" *Cell* 31(3 Pt 2):543–551 (Dec. 1982).

Tsukui et al., "A monoclonal antibody with broad reactivity to human interferon–α subtypes useful for purification of leukocyte–derived interferon" *Microbiology & Immunology* 30(11):1129–1139 (1986).

Ullrich et al., "Nucleotide sequence of a portion of human chromosome 9 containing a leukocyte interferon gene cluster" *Journal of Molecular Biology* 156(3):467–486 (Apr. 15, 1982).

Uze et al., "Genetic transfer of a functional human interferon α receptor into mouse cells: cloning and expression of its cDNA" *Cell* 60:225–234 (1990).

Weissmann et al., "Structure and expression of human INF–α genes" *Philosophical Transactions of the Royal Society of London—Series B: Biological Sciences* 299(1094) : 7–28 (Sep. 24, 1982).

Wetzel, R., "Assignment of the disulphide bonds of leukocyte interferon" *Nature* 289 (5798):606–607 (Feb. 12, 1981).

Whaley et al., "Identification and cellular localization of unique interferon mRNA from human placenta" *Journal of Biological Chemistry* 269(14):10864–10868 (Apr. 8, 1994).

Zhang et al., "Neuregulin–3 (NRG3): A novel neural tissue–enriched protein that binds and activates ErbB4" *Proc. Natl. Acad. Sci. USA* 94:9562–9567 (Sep. 22, 1997).

Zhang et al., "STAT3 participates in transcriptional activation of the C–reactive protein gene by interleukin–6" *Journal of Biological Chemistry* 271(16):9503–9509 (Apr. 19, 1996).

<208 208 residues, 0 stop; molecular weight: 24414.41

```
        10         20         30         40         50         60         70
         |          |          |          |          |          |          |
  1 —MIIKHFFGTVLVLLASTTIFSLDLKLIIFQQRQVNQESLKLLNKLQTLSIQQCLPHRKNFLLPQKSLSPQ
    v v                v v
        80         90        100        110        120        130        140
         |          |          |          |          |          |          |
 71 —QYQKGHTLAILHEMLQQIFSLFRANISLDGWEENHTEKFLIQLHQQLEYLEALMGLEAEKLSGTLGSDNL
              v v
       150        160        170        180        190        200
         |          |          |          |          |          |
141 —RLQVKMYFRRIHDYLENQDYSTCAWAIVQVEISRCLFFVFSLTEKLSKQGRPLNDMKQELTTEFRSPR
    v v
```

FIG. 1

DNA50960

CTTAGATATTAAACTGATAAGGATAAGATATAAAATAATTAAGATTGCTGATATATGTTT
TAAAATTAATTATTGCTCAAGCATTGTGACAATTACAGTTCTAATTGAGTTTTAAA
TTTAGTAGTTTGTAGGTATTTAAGTTTTGCCCCTGAATTCTTATAGGTGCTGATAAGC
CTTTGGTTAAGTTTACTCCATGAAAGACTATTACTGAAAAAAATGTAATCTCAATAAAA
GAACTTTAATAAGCTTGACTAAATATTAGAAAGCACATGTGTTCAGTGAAACTTTGTA
TATAATGAATAGAATAATAAAAGATTATGTTGGATGACTAGTCTGTAATTGCCTCAAGGA
AAGCATACAATGAATAAGTTATTTTGGTACTTCCTCAAAATAGCCAACACAATAGGAAA
TGGAGAAAATGTACTCTGAACACCATGAAACCTGAAAATCTAATGTGTAAACTT
GGAGAAATGACATTAGAAAAGCAACAAAAGAGAACACTCTCAAATAATCTGAG
ATGCATGAAAGGCAAACATTCACTAGAGCTGAATTTCCCTAAGTCTATGCAGGATAAG
TAGCATATTTGACCTTCACC
><Met (trans=1-s, dir=f, res=1)>
ATGATTATCAAGCACTTCTTTGGAACTGTGTTGGTGCTGCTGGCCTCTACCACTATCTTC
TCTCTAGATTTGAAACTGATTATCTCCAGCAAGTGAATCAAGACAAGTGAATCAAGAAAGTTTAAAA
CTCTGAATAAGTTGCAAACCTTGTCAATTCAGCAGTGTCTACCACACAGAAAAACTTT
CTGCTTCCTCAGAAGTCTTGAGTCCTCAGCAGTCCTCAGCAGTACCAAAAGGACACACTCTGGCCATT
CTCCATGAGATGCTTCAGCAGATCTTCAGCCTTCATTCAGGGCAAATATTCTCTGATGGT
TGGGAGGAAAACCACAGGAGAGAATTCCTCATTCAACTTCATCAACAGCTAGAATACCTA
GAAGCACTCATGGACTGGAAGCAGAGAAGCTAAGTGGTACTTTGGGTAGTGATAACCTT
AGATTACAAGTTAAAATGTACTTCCGAAGATCCATGATTACCTGAAAACCAGGACTAC
AGCACCTGTGCCTGGGCCATTGTCCAAGTAGAAATCAGCCGATGTCTGTCTTTGTGTTC
AGTCTCACAGAAAAACTGAGCAAAACTGAGCCCGAGGTAGGTGGAGGACTAGAGGACTTCTCCAGACATGAT
ACTACAGAGTTTAGAAGCCCGAGGTAGGTGGAGGACTAGAGGACTTCTCCAGACATGAT
TCTTCATGAGTGGTAATACAATTTATAGTACAATCACATTGCTTTGATTTGTGTATAT
ATATATTATCTGAGTTTTAAGATTGTGCATATTGACCACAATTGTTTTTATTTGTAAT
GTGGCTTTATATATTCTATCCATTTAAATTGTTGTATGTCAAAATAAATTCATTAATA
TGGTTGATTCTTCAAAAAAAAAAAAAAAAAAAAAAA

```
1001  AGCAGAGAAG CTAAGTGGTA CTTTGGGTAG TGATAACCTT TTAAAATGTA CTTCCGAAGG ATCCATGATT ACCTGGAAAA CCAGGACTAC
      TCGTCTCTTC GATTCACCAT GAAACCCATC ACTATTGGAA AATTTTACAT GAAGGCTTCC TAGGTACTAA TGGACCTTTT GGTCCTGATG
 128   A  E  K   L  S  G   T  L  G  S   D  N  L   K  N  Y   F  R  R    I  H  D  Y   L  E  N    Q  D  Y

1101  AGCACCTGTG CCTGGGCCAT TGTCCAAGTA GAAATCAGCC CTTTGTGTTC AGTCTCACAG AAAAACTGAG CAAACAAGGA AGACCCTTGA
      TCGTGGACAC GGACCCGGTA ACAGGTTCAT CTTTAGTCGG GAAACACAAG TCAGAGTGTC TTTTTGACTC GTTTGTTCCT TCTGGGAACT
 161   S  T  C   W  A  I   V  Q  V   E  I  S  R   F  V  F   S  L  T   E   K  L  S   K  Q  G    R  P  L  N

1201  ACGACATGAA GCAAGAGCTT ACTACAGAGT TTAGAAGCCC GAGGTAGGTG AGGACTTCTC CAGACATGAT TCTTCATAGA GTGGTAATAC
      TGCTGTACTT CGTTCTCGAA TGATGTCTCA AATCTTCGGG CTCCATCCAC TCCTGAAGAG GTCTGTACTA AGAAGTATCT CACCATTATG
 195   D  N  K   Q  E  L    T  T  E  F    R  S  P   R  Q     E  D  F  S   R  H  D    L  H  R   V  V  M

1301  AATTTATAGT ACAATCACAC TGCTTTGATT ATATATTTAT CTGAGTTTTA AGATTGTGCA TATTGACCAC AATTGTTTTT ATTTTGTAAT
      TTAAATATCA TGTTAGTGTG ACGAAACTAA TATATAAATA GACTCAAAAT TCTAACACGT ATAACTGGTG TTAACAAAAA TAAACATTA

1401  GTGGCTTTAT ATATTCTATC CATTTTAAAT TGTTTGTATG TCAAAATAAA TTCATTAATA TGGTTGATTC TCAAAAAAAA AAAAAAAAAA
      CACCGAAATA TATAAGATAG GTAAAATTTA ACAAACATAC AGTTTTATTT AAGTAATTAT ACCAACTAAG AGTTTTTTTT TTTTTTTTTT

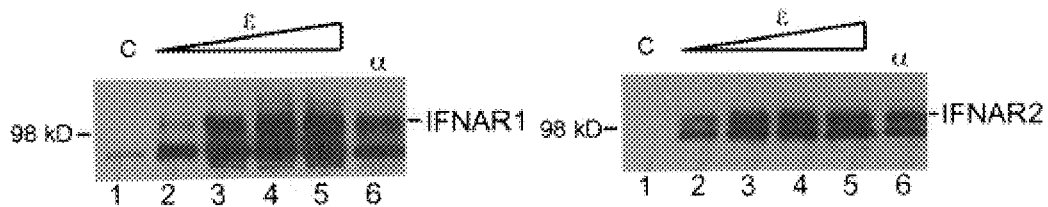
FIG. 8A
FIG. 8B
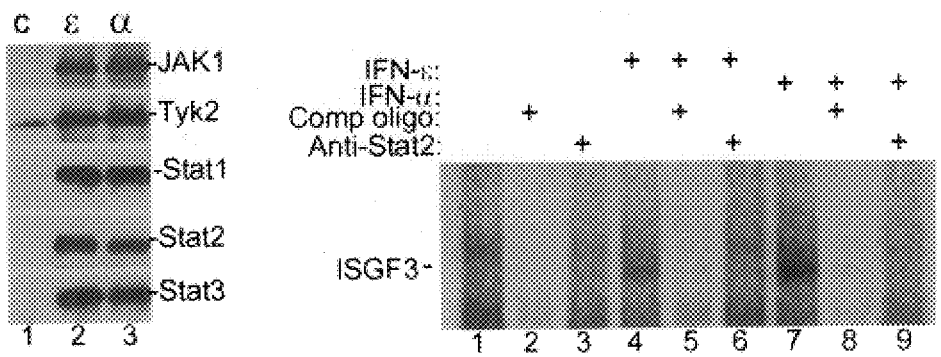
FIG. 8C
FIG. 8D
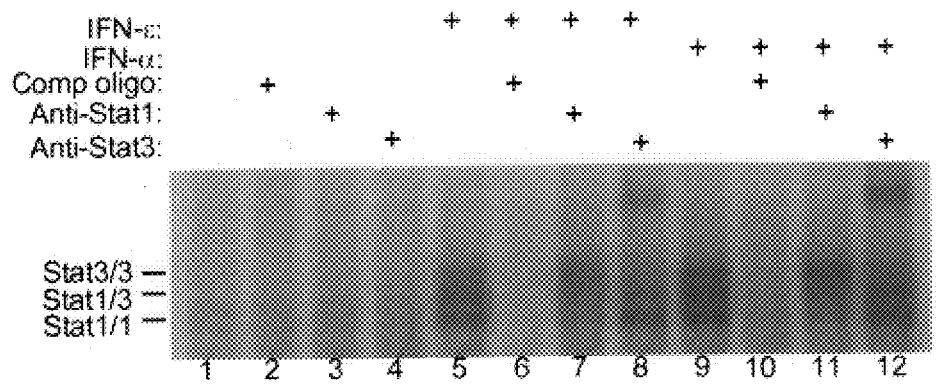
FIG. 8E
FIG. 8F

HUMAN INTERFERON-EPSILON: A TYPE I INTERFERON

The present application is a 371 of PCT/US98/25672 filed on Dec. 3, 1998, which claims the benefit of priority under 35 U.S.C. § 119 to provisional application Nos. 60/106,463 filed Oct. 30, 1998; Ser. No 60/084,045 filed May 4, 1998 and Ser. No. 60/067,897 filed Dec. 8, 1997.

FIELD OF THE INVENTION

The present invention relates generally to the identification of a novel member of the type I interferon family. More specifically, the present invention concerns the isolation of a novel nucleic acid encoding a new and distinct type I interferon, termed interferon-epsilon (IFN-ε).

BACKGROUND OF THE INVENTION

Interferons are relatively small, single-chain glycoproteins released by cells invaded by viruses or certain other substances. Interferons are presently grouped into three major classes, designated leukocyte interferon (interferon-alpha, α-interferon, IFN-α), fibroblast interferon (interferon-beta, β-interferon, IFN-β), and immune interferon (interferon-gamma, γ-interferon, IFN-γ). In response to viral infection, lymphocytes synthesize primarily α-interferon (along with a lesser amount of a distinct interferon species, commonly referred to as omega interferon, IFN-ω), while infection of fibroblasts usually induces β-interferon. α- and β-interferons share about 20–30 percent amino acid sequence homology. Thus, the gene for human IFN-β lacks introns, and encodes a protein possessine 29% amino acid sequence identity with human IFN-αI, suggesting that IFN-α and IFN-β genes have evolved from a common ancestor (Taniguchi et al., *Nature* 285, 547–549 (1980)). By contrast, IFN-γ is not induced by viral infection, rather, is synthesized by lymphocytes in response to mitogens, and is scarcely related to the other two types of interferons in amino acid sequence. Interferons-α, β and ω are known to induce MHC Class I antigens, and are referred to as type I interferons, while IFN-γ induces MHC Class II antigen expression, and is also referred to as type II interferon.

A large number of distinct genes encoding different species of IFNs-α have been identified. Alpha interferon species identified previously fall into two major classes, I and II, each containing a plurality of discrete proteins (Baron et al., *Critical Reviews in Biotechnology* 10, 1790190 (1990); Nagata et al., *Nature* 287, 401–408 (1980); Nagata et al., *Nature* 284, 316–320 (1980); Streuli et al., *Science* 209, 1343–1347 (1980); Goeddel et al., *Nature* 290, 20–26 (1981); Lawn et al., *Science* 212, 1159–1162 (1981); Ullrich et al., *J. Mol. Biol.* 156, 467–486 (1982); Weissmann et al., *Phil. Trans. R. Soc. Lond.* B299, 7–28 (1982); Lund et al., *Proc. Natl. Acad. Sci.* 81, 2435–2439 (1984); Capon et al., *Mol. Cell. Biol.* 5, 768 (1985)). The various IFN-α species include IFN-αA (IFN-α2), IFN-αB, IFN-αC, IFN-αC1, IFN-αD (IFN-α1), IFN-αE, IFN-αF, IFN-αG, IFN-αH, IFN-αI, IFN-αJ1, IFN-αJ2, IFN-αK, IFN-αL, IFN-α4B, IFN-α5, IFN-α6, IFN-α74, IFN-α76 IFN-α4a), IFN-α88, and alleles of these species. According to our current knowledge, the IFN-α family consists of 13 expressed alleles producing 12 different proteins that exhibit remarkably different biological activity profiles. Pestka, S., *Semin. Oncol.* 24(suppl. 9), S9–4–S9–17 (1997).

Interestingly. while only a single human IFN-β gene has been unequivocally identified, bovine IFN-β is encoded by a family of five or more homologous, yet distinct genes.

Interferons were originally produced from natural sources, such as buffy coat leukocytes and fibroblast cells, optionally using known inducing agents to increase interferon production. Interferons have also been produced by recombinant DNA technology.

The cloning and expression of recombinant IFN-αA (rIFN-αA, also known as IFN-α2) was described by Goeddel et al., *Nature* 287, 411 (1980). The amino acid sequences of rIFNs-αA, B, C, D, F, G, H, K and L, along with the encoding nucleotide sequences, are described by Pestka in *Archiv. Biochem. Biophys.* 221, 1 (1983). The amino acid sequences and the underlying nucleotide sequences of rIFNs-αE, I and J are described in British Patent Specification No. 2,079,291, published Jan. 20, 1982. Hybrids of various IFNs-α are also known, and are disclosed, e.g. by Pestka et al., supra. Nagcata et al., *Nature* 284, 316 (1980), described the expression of an IFN-α gene, which encoded a polypeptide (in non-mature form) that differs from rIFN-αD by a single amino acid at position 114. Similarly, the cloning and expression of an IFN-α gene (designated as rIFN-α2) yielding a polypeptide differing from rIFN-αA by a single amino acid at position 23, was described in European Patent Application No. 32 134, published Jul. 15, 1981.

The cloning and expression of mature rIFN-β is described by Goeddel et al., *Nucleic Acids Res.* 8, 4057 (1980).

The cloning and expression of mature rIFN-γ are described by Gray et al., *Nature* 295, 503 (1982).

IFN-ω has been described by Capon et al., *Mol. Cell. Biol.* 5, 768 (1985).

IFN-τ has been identified and disclosed by Whaley et al., *J. Biol. Chem.* 269, 10864–8 (1994).

All of the known IFNs-α, -β, and -γ contain multiple cysteine residues. These residues contain sulfhydryl sidechains which are capable of forming intermolecular disulfide bonds. For example, the amino acid sequence of mature recombinant rIFN-αA contains cysteine residues at positions 1, 29, 98 and 138. Wetzel et al., *Nature* 289, 606 (1981), assigned intramolecular disulfide bonds between the cysteine residues at positions 1 and 98, and between the cysteine residues at positions 29 and 138.

Antibodies specifically binding various interferons are also well known in the art. For example, anti-α-interferon agonist antibodies have been reported by Tsukui et al., *Microbiol. Immunol.* 30, 112901139 (1986); Duarte et al., *Interferon-Biotechnol.* 4, 221–232 (1987); Barasoaian et al., *J. Immunol.* 143, 507–512 (1989); Exley et al., *J. Gen. Virol.* 65, 2277–2280 (1984); Shearer et al., *J. Immunol.* 133, 3096–3101 (1984); Alkan et al., Ciba Geigy Foundation Symposium 119, 264–278 (1986); Noll et al., Biomed. Biochim. Acta 48, 165–176 (1989); Hertzog et al., *J. Interferon Res.* 10 (Suppl. 1) (1990); Kontsek et al., *J. Interferon Res.* (special issue) 73–82 (1991), and U.S. Pat. No. 4,423, 147 issued Dec. 27, 1983.

The actions of type I interferons appear to be mediated by binding to the IFN-α a receptor complex on the cell surface. This receptor is composed of at least two distinct subunits identified as IFN-αR1 (Uze et al., *Cell* 60, 225–234 [1990]) and IFN-αR2 (Novick et al. *Cell* 77, 391–400 [1994]), each having 2 and 3 spliced variants, respectively. IFN-αR2 is the binding subunit of the known type interferons, whereas IFN-αR1 contributes to higher affinity binding and signaling. The engagement of receptors by ligand binding activates Janus family kinases (JAK) and protoplasmic latent signal transducers and activators of transcription (STAT) proteins by tyrosine phosphorylation. Activated STATs translocate to the nucleus in forms of complexes and interact with their cognitive enhancer elements of IFN-stimulated genes (ISGs). leading to a corresponding transcription activation and biological responses. Darnell et al., *Science* 264, 1415–21 (1994). However, despite similarities in their binding properties, the biological responses stimulated by type I interferons are significantly different.

Interferons have a variety of biological activities, including antiviral, immunoregulatory and antiproliferative properties, and are, therefore, of great interest as therapeutic agents in the control of cancer, and various viral diseases. Interferons have been implicated in the pathogenesis of various autoimmune diseases, such as systemic lupus erythematoses, Behcet's disease, insulin-dependent diabetes mellitus (IDDM, also referred to as type I diabetes). It has been demonstrated in a transgenic mouse model that β cell expression of IFN-α can cause insulitis and IDDM, and IFN-α antagonists (including antibodies) have been proposed for the treatment of IDDM (WO 93/04699, published Mar. 18, 1993). Impaired IFN-γ and IFN-α production has been observed in multiple sclerosis (MP) patients. An acid-labile IFN-α has been detected in the serum of many AIDS patients, and it has been reported that the production of IFN-γ is greatly suppressed in suspensions of mitogen-stimulated mononuclear cells derived from AIDS patients. For a review see, for example, Chapter 16, "The Presence and Possible Pathogenic Role of Interferons in Disease", In: *Interferons and other Regulatory Cytokines*, Edward de Maeyer (1988, John Wilet and Sons publishers). Alpha and beta interferons have been used in the treatment of the acute viral disease herpes zoster (T. C. Merigan et al., *N. Engl. J. Med.* 298, 981–987 (1978); E. Heidemann et al., *Onkologie* 7, 210–212 (1984)), chronic viral infections, e.g. hepatitis B infections (R. L. Knobler el al., *Neurology* 34, 1273078 (1984); M. A. Faerkkilae et al., *Act. Neurol. Sci.* 69, 184–185 (1985)). rIFN-α-2a (Roferon®, Roche) is an injection formulation indicated in use for the treatment of hairy cell leukemia and AIDS-related Kaposi's sarcoma. Recombinant IFN-α-2b (Intron® A. Schering) has been approved for the treatment of hairy cell leukemia, selected cases of condylomata acuminata, AIDS-related Kaposi's sarcoma, chronic hepatitis Non-A, Non-B/C, and chronic helatitis B infections is certain patients. IFN-γ-1b (Actimmune®, Genentech. Inc.) is commercially available for the treatment of chronic granulomatous disease.

For further information about the biologic activities of type I IFNs see, for example, Pfeffer, *Semin. Oncol.* 24(suppl 9), S9–63–S9–69 (1997).

SUMMARY OF THE INVENTION

Applicants have identified a cDNA clone (designated in the present application as "DNA50960") that encodes a novel human interferon polypeptide, which is now designated as human IFN-ε.

In one embodiment, the invention provides an isolated nucleic acid molecule comprising DNA having at least a 95% sequence identity to (a) a DNA molecule encoding a novel human interferon polypeptide originally designated PRO655, and hereinafter also referred to as IFN-ε, comprising the sequence of amino acids from about 22 to 189 of FIG. 1 (SEQ ID NO:1), or (b) the complement of the DNA molecule of (a). In one aspect, the isolated nucleic acid comprises DNA encoding a new interferon polypeptide having at least amino acid residues 22 to 189 of FIG. 1 (SEQ ID NO:1), or is complementary to such encoding nucleic acid sequence, and remains stably bound to it under at least moderate, and optionally, under high stringency conditions.

In another embodiment, the isolated nucleic acid molecule encodes the full-length polypeptide represented in FIG. 1 (SEQ. ID. NO:1), with or without the putative signal peptide at amino acids 1–21, and with or without the initiating methionine, or is the complement of such DNA molecule. In a further embodiment, the isolated nucleic acid molecule comprises DNA having at least a 95% sequence identity to (a) DNA molecule encoding the same mature polypeptide encoded by the human interferon protein cDNA in ATCC Deposit No.209509 (DNA50960–1224), deposited on Dec. 3, 1997.

In another embodiment, the invention provides a vector comprising DNA (as hereinabove defined) encoding a novel interferon-ε polypeptide. A host cell comprising such a vector is also provided. By way of example, the host cells may be CHO cells, *E. coli*, or yeast (including *Saccharomyces cerevisiae* and other yeast strains). A process for producing the new interferon polypeptides of the present invention is further provided and comprises culturing host cells under conditions suitable for expression of the desired interferon polypeptide, and recovering the interferon from the cell culture.

In another embodiment, the invention provides novel, isolated interferon-ε polypeptides. In particular, the invention provides isolated a native interferon-ε polypeptide, which in one embodiment, includes an amino acid sequence comprising residues 22 to 189 of FIG. 1 (SEQ ID NO:1). In another embodiment, the IFN-ε polypeptide has at least about 95% sequence identity with the native human IFN-ε polypeptide specifically disclosed in the present application. and preferably retains the pair of cysteine residues at amino acid positions 32 and 142. Both glycosylated and unglycosylated forms of the IFN-ε polypeptides are included.

In another embodiment, the invention provides chimeric molecules comprising, a novel interferon-ε polypeptide herein fused to a heterologous polypeptide or amino acid sequence. An example of such a chimeric molecule comprises an interferon-ε polypeptide fused to an epitope tag sequence or an immunoglobulin heavy or light chain constant region sequence, e.g. the Fc region of an immunoglobulin.

In another embodiment, the invention provides an antibody which specifically binds to a novel interferon-ε polypeptide disclosed herein. Optionally, the antibody is a monoclonal antibody.

In a further aspect, the present invention concerns compositions comprising an effective amount of an IFN-ε polypeptide, or an agonist thereof, in admixture with a pharmaceutically acceptable carrier. The composition may, for example, be used for the inhibition of neoplastic cell growth, e.g. for the treatment of various tumors, including cancers, such as leukemias, AIDS-related Kaposi's sarcoma, etc. In a particular embodiment, the composition comprises a cytostatic amount of an IFN-ε polypeptide, or an agonist thereof. In a preferred embodiment, the composition comprises a growth inhibitory amount of an IFN-ε polypeptide, or an agonist thereof. In another preferred embodiment, the composition comprises a cytotoxic amount of an IFN-ε polypeptide, or an agonist thereof. In yet another preferred embodiment, the composition comprises IFN-ε in an amount capable of evoking apoptosis of a target cell. Optionally, the compositions may contain one or more additional growth inhibitory and/or cytotoxic and/or other chemotherapeutic agents. In a further embodiment, the compositions may be used to treat viral infections, such as, the acute viral disease zoster, chronic viral infections, e.g. chronic hepatitis non-A, non-B and chronic hepatitis B infections, etc. In a still further embodiment, the compositions are used to upregulate the immune system.

In another aspect, the invention concerns a method for inhibiting the growth of a tumor cell comprising exposing the cell to an effective amount of an IFN-ε polypeptide, or an agonist thereof. In a particular embodiment, the agonist is an anti-IFN-ε agonist antibody. In another embodiment, the agonist is a small molecule that mimics the biological activity of a native IFN-ε polypeptide. The treatment may be performed in vitro or in vivo.

In yet another aspect, the invention concerns a method for treating a viral infection comprising administering a therapeutically effective amount of an IFN-ε polypeptide, or an agonist thereof.

In a further aspect, the invention concerns a method for upregulation of the immune system comprising administering a therapeutically effective amount of an IFN-ε polypeptide, or an agonist thereof.

In a still further embodiment, the invention concerns an article of manufacture, comprising:
  a container; and
  a composition comprising an active agent contained within the container; wherein the composition is effective for inhibiting neoplastic cell growth, e.g. growth of tumor cells, and/or to cause apoptosis of such cells, and the active agent in the composition is an IFN-ε polypeptide, or an agonist thereof. In a particular embodiment, the aoonist is an anti-IFN-ε agonist antibody. In another embodiment, the agonist is a small molecule that mimics the biological activity of a native IFN-ε polypeptide.

Similarly, articles of manufacture comprising IFN-ε in an amount effective to treat viral infections and/or to upregulate the immune system are within the scope of the invention.

In a further embodiment, the invention concerns a method for screening compounds for anti-tumor activity. In one aspect, the screening assay is designed to identify agonists of a native IFN-ε polypeptide by testing the ability of a candidate compound to inhibit the growth of a tumor cell the growth of which has been inhibited by a native IFN-ε polypeptide, or a fragment thereof. In another embodiment, the screening assay is designed to identify compounds that are capable of enhancing the expression level of a native IFN-ε polypeptide in a biological cell sample in which the expression of level of the native protein has been determined to be subnormal.

In yet another embodiment, the invention concerns a method for the prognosis or diagnosis of tumor in a mammal, comprising determining in a test sample taken from the mammal, the expression level of an IFN-ε polypeptide, and comparing the result with the expression level of the same polypeptide in a test sample taken from a healthy mammal of the same species. under identical conditions. Subnormal expression of any of the IFN-ε gene may be indicative that the mammal tested has a tendency to develop a tumor, or has already developed tumor.

The invention firther concerns compositions comprising an effective amount of an IFN-ε antagonist, e.g. an antagonist anti-IFN-ε antibody or a small molecule antagonist. Such compositions may be used for the treatment of conditions associated with the overexpression of IFN-ε. Without limitation, such conditions include autoimmune diseases, such as systemic lupus erythematoses, Behcet's disease, and insulin-dependent diabetes mellitus (IDDM, also referred to as type I diabetes). Methods for treating such conditions are also within the scope of the invention.

BRIEF DESCRIPTION OF THE DRAWINGS

FIG. 1 shows the derived amino acid sequence of a native sequence human interferon-ε polypeptide, originally designated PRO655 (SEQ ID NO:1). Amino acids 1 to 21 have been identified as a putative signal sequence, using the method of G. von Heijne, *N.A.R.* 14, 4683 (1986).

FIG. 2 shows the nucleotide sequence of a native sequence PRO655 interferon-ε cDNA (SEQ ID NO:2). The ATG start codon encoding the N-terminal initiating methionine residue is indicated.

FIGS. 3A–B show the nucleotide sequence (SEQ ID NO:2), complimentary sequence (SEQ ID NO:3) and the derived amino acid sequence (SEQ ID NO:1) of the native sequence human interferon-ε polypeptide PRO655.

FIG. 4 shows the protein sequence analysis of IFN-ε and comparison with Type I IFNs: IFN-α2 (SEQ ID NO:7), IFN-β (SEQ ID NO:9), IFN-ω (SEQ ID NO:8).

FIG. 6 shows the nucleotide sequence (SEQ ID NO:10), complimentary sequence (SEQ ID NO:11) and the deduced amino acid sequence (SEQ ID NO:12) of DNA49668 used in the cloning of DNA50960.

FIGS. 8A–F illustrate that IFN-ε activates tyrosine phosphorylation of IFN-αR1, IFN-αR2 and components in the JAK-STAT pathway. (A) U266 cells were untreated (lane 1) or treated with Histidine (His)-tagged IFN-ε (IFN-ε$^{His}$) of 2 nM, 20 nM, 50 nM and 100 nM (lanes 2, 3, 4, 5, respectively), or with IFN-α$_{2a}$ at $10^3$ U/ml (lane 6, $10^3$ U/ml~0.22 nM) for 10 minutes. The cells were lysed and immunoprecipitated by anti-IFN-αR1 antibody (2E1.5.2), probed with peroxidase-conjugated anti-phosphotyrosine antibody 4G10. The molecular weight (MW, in kDa) is indicated on the left. The band below 98 kD is Stat-1α as analyzed by reprobing with anti-Stati antibodies (data not shown). (B) Same treatment as described in (A) except that the cell lysates were immunoprecipitated by anti-IFN-αR2 antibody (3B7.22.7). Equal loading was confirmed by re-probing the blots with corresponding antibodies (data not shown). © U266 cells were untreated (lane 1), treated with 20 nM of IFN-ε$^{His}$ (lane 2), or with $10^3$ U/ml of IFN-α$_{2a}$ (lane 3) for 15 minutes. The cells were lysed and immunoprecipitated by antibodies against JAK1, Tyk2, Stat1, Stat2 and Stat3, and probed with anti-phosphotyrosine antibody 4G10. Each blot was stripped and probed with antibodies against the corresponding protein and equal loading was confirmed (not shown). (D-E) IFN-ε activates formation of ISGF3 and SIF transcription factor complexes. HeLa cells were either untreated or treated with IFN-ε$^{His}$ (20 nM) or with IFN-α$_{2a}$ (4,000 U/ml) for 45 minutes. Nuclear extract (8 μg of protein) was incubated with about 200 fmol of $^{32}$P-labeled ISRE (D) or SIE (E) oligonucleotides and analyzed by EMSA. In competition experiments (labeled as "Comp oligo"), 50-fold molar excess of cold oligonucleotides were included in the binding reaction. In supershift experiments (labeled as "anti-Stat"), 1 μg of indicated antibody was employed in the binding reaction. (F) IFN-αR1 and IFN-αR2 are necessary components for IFN-ε induced signaling. MOLT-4 cells ($10^7$ in 1 ml) were pretreated with 10 μg/ml of anti-IFN-αR1 antibody 2E1.5.2 (lanes 3 and 7), or with control anti-HER2 antibody (lanes 5 and 10) for 30 minutes at room temperature and subjected to either no treatment (lane 1) or treatment with IFN-ε$^{His}$ (lanes 2–5) or with IFN-α$_{2a}$ (lanes 6–9). The cells were lysed and immunoprecipitated by anti-Stat2 antibody probed with peroxidase-conjugated anti-phosphotyrosine antibody 4G10.

DETAILED DESCRIPTION OF THE PREFERRED EMBODIMENTS

1. Definitions

Figure 5:
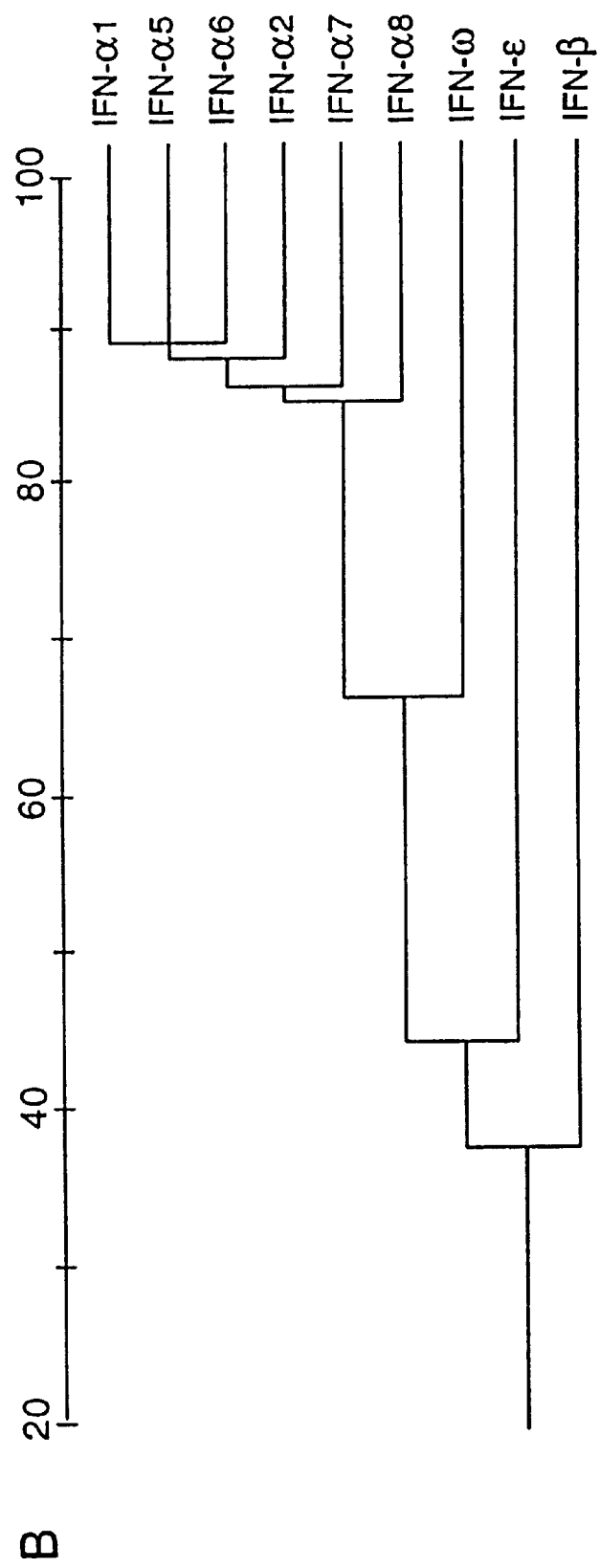
FIG. 5 is a phylogenetic tree of representative human IFNs, with 6 IFN-α species included to highlight the relatioship of the IFN-α family members.

The terms "interferon-ε (IFN-ε)", "IFN-ε polypeptide", "PRO655 polypeptide" and "PRO655" when used herein encompass native sequence IFN-ε and IFN-ε variants (which are further defined herein). The novel IFN-ε polypeptide, originally designated PRO655, may be isolated from a variety of sources, such as from human tissue types or from another source, or prepared by recombinant or synthetic methiods, or by any combination of these or similar techniques.

A "native sequence interferon-ε (IFN-ε)", or "native sequence IFN-ε polypeptide" or "native sequence PRO655 polypeptide" or "native sequence PRO655" which terms are used interchangeably, comprises a polypeptide having the same amino acid sequence as an IFN-ε polypeptide derived from nature. Such native sequence IFN-ε can be isolated from nature or can be produced by recombinant or synthetic means. The term "native sequence IFN-ε" specifically encompasses naturally-occurring truncated forms of the IFN-ε polypeptide, naturally-occurring variant forms (e.g. alternatively spliced forms) and naturally-occurring allelic variants of the native sequence interferon polypeptide herein. In one embodiment of the invention, the native sequence IFN-ε is a mature or full-length native sequence IFN-ε comprising amino acids 22 to 208 of FIG. 1 (SEQ ID NO:1).

"IFN-ε variant" means an active IFN-ε as defined below encoded by a nucleic acid comprising DNA having at least about 80% nucleic acid sequence identity to (a) a DNA molecule encoding an IFN-ε polypeptide, with or without its signal sequence, or (b) the complement of the DNA molecule of (a). In a particular embodiment, the "IFN-ε variant" has at least about 80% amino acid sequence identity with the IFN-ε having the deduced amino acid sequence shown in FIG. 1 (SEQ ID NO:1) for a full-length native sequence IFN-ε. Such IFN-ε variants include, for instance, IFN-ε polypeptides wherein one or more amino acid residues are added, or deleted at the N- or C-terminus of the sequence of FIG. 1 (SEQ ID NO:1). Preferably, the nucleic acid or amino acid sequence identity is at least about 85%, more preferably at least about 90%, and even more preferably at least about 95%.

"Percent (%) amino acid sequence identity" with respect to the IFN-ε sequences identified herein is defined as the percentage of amino acid residues in a candidate sequence that are identical with the amino acid residues in the IFN-ε sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. In a preferred embodiment, alignment is done using the ALIGN software.

"Percent (%) nucleic acid sequence identity" with respect to the IFN-ε coding sequences identified herein is defined as the percentage of nucleotides in candidate sequence that are identical with the nucleotides in the IFN-ε coding sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the ALIGN software is used to determine nucleic acid sequence identity.

In a particularly preferred embodiment, percent (%) amino acid sequence identity" with respect to the IFN-ε polypeptides identified herein is defined as the percentage of amino acid residues in a candidate sequence that are identical with the amino acid residues in the IFN-ε sequence, after aligning the sequences and introducing gaps, if necessary, to achieve the maximum percent sequence identity, and not considering any conservative substitutions as part of the sequence identity. The % identity values used herein are generated by WU-BLAST-2 which was obtained from [Altschul et al., *Methods in Enzymology*, 266: 460–480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The term "positives", in the context of sequence comparison performed as described above. includes residues in the sequences compared that are not identical but have similar properties (e.g. as a result of conservative substitutions). The % value of positives is determined by the fraction of residues scoring a positive value in the BLOSUM 62 matrix divided by the total number of residues in the longer sequence, as defined above.

In a similar manner, in a particularly preferred embodiment, "percent (%) nucleic acid sequence identity" with respect to the coding sequence of IFN-ε is defined herein as the percentage of nucleotide residues in a candidate sequence that are identical with the nucleotide residues in the IFN-ε coding sequence. The identity values used herein were generated by the BLASTN module of WU-BLAST-2 set to the default parameters, with overlap span and overlap fraction set to 1 and 0.125, respectively.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the IFN-ε natural environment will not be present. Ordinarily, however, isolated polypeptide will be prepared by at least one purification step.

An "isolated" nucleic acid molecule encoding IFN-ε is a nucleic acid molecule that is identified and separated from at least one contaminant nucleic acid molecule with which it is ordinarily associated in the natural source of the IFN-ε-encoding nucleic acid. An isolated nucleic acid molecule is other than in the form or setting in which it is found in nature. Isolated nucleic acid molecules encoding IFN-ε therefore are distinguished from the IFN-ε-encoding nucleic acid molecule as it exists in natural cells. However, an isolated nucleic acid molecule encoding IFN-ε includes nucleic acid molecules contained in cells that ordinarily express IFN-ε where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate). 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Labo-* ratory Manual, New York: Cold Spring Harbor Press, 1989, and include the use of washing solution and hybridization conditions (e.g., temperature, ionic strength and %SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising an IFN-ε polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Tumor", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, endometrial carcinoma, salivary gland carcinoma, kidney cancer, vulval cancer, thyroid cancer, hepatic carcinoma and various types of head and neck cancer.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In tumor (e.g. cancer) treatment, a therapeutic agent may directly decrease the pathology of tumor cells, or render the tumor cells more susceptible to treatment by other therapeutic agents, e.g. radiation and/or chemotherapy. Similarly, in the treatment of virus infections, the therapeutic agent may treat the infection directly, or increase the efficacy of other antiviral treatments, e.g. by upregulating the immune system of the patient.

"Chronic" administration refers to administration of the agent(s) in a continuous mode as opposed to an acute mode, so as to maintain the initial biological effect for an extended period of time.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

"Mammal" for purposes of treatment refers to any animal classified as a mammal, including humans, domestic and farm animals, and zoo, sports, or pet animals, such as horses, sheep, cows, pigs, dogs, cats, etc. Preferably, the mammal is human.

An "effective amount" of an IFN-ε polypeptide disclosed herein or an agonist thereof, in reference to inhibition of neoplastic cell growth, is an amount capable of inhibiting, to some extent, the growth of target cells. The term includes an amount capable of invoking a growth inhibitory, cytostatic and/or cytotoxic effect and/or apoptosis of the target cells.

A "therapeutically effective amount", in reference to the treatment of tumor, refers to an amount capable of invoking one or more of the following effects: (1) inhibition, to some extent, of tumor growth, including, slowing down and complete growth arrest; (2) reduction in the number of tumor cells; (3) reduction in tumor size; (4) inhibition (i.e., reduction, slowing down or complete stopping) of tumor cell infiltration into peripheral organs; (5) inhibition (i.e., reduction, slowing down or complete stopping) of metastasis; (6) enhancement of anti-tumor immune response, which may, but does not have to, result in the regression or rejection of the tumor; and/or (7) relief, to some extent, of one or more symptoms associated with the disorder.

In "effective amount" in the context of antiviral treatment is an amount capable of at least partial killing of the target virus population.

A "therapeutically effective amount" in the context of antiviral activity is an amount capable of invoking one or more of the following effects: (1) at least partial killing of the virus causing the infection; (2) enhancement of anti-viral immune response; (3) relief, to some extent, of one or more symptoms associated with the disorder.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Administration "in combination with" one or more further therapeutic agents includes simultaneous (concurrent) and consecutive administration in any order.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of tumor, e.g. cancer. Examples of chemotherapeutic agents include adriamycin, doxorubicin, epirubicin, 5-fluorouracil, cytosine arabinoside ("Ara-C"), cyclophosphamide thiotepa, busulfan, cytoxin, taxoids, e.g.

paclitaxel (Taxol, Bristol-Myers Squibb Oncology, Princeton, N.J.), and doxetaxel (Taxotere, Rhone-Poulenc Rorer, Antony, Rnace), toxotere, methotrexate, cisplatin melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially tumor, e.g. cancer cell, either in vitro or in vivo. Thus, the growth inhibitory agent is one which significantly reduces the percentage of the target cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al. (WB Saunders: Philadelphia, 1995), especially p. 13.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormnone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactooen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-(G-CSF); interleukins (ILs) such as IL-1, IL-1α, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g. Wilman, "Prodrugs in Cancer Chemotherapy", *Biochenuical Society Transactions*, 14, pp. 375–382, 615th Meeting Belfast (1986) and Stella et al., "Prodrugs: A Chemical Approach to Targeted Drug Delivery," Directed Drug Delivery, Borchardt et al., (ed.), pp. 247–267, Humana Press (1985). The prodrugs of this invention include, but are not limited to, phosphate-containing prodrugs, thiophosphate-containing prodrugs, glycosylated prodrugs or optionally substituted phenylacetamide-containing prodrugs, 5-fluorocytosine and other 5-fluorouridine prodrugs which can be derivatized into a prodrug form for use in this invention include, but are not limited to, those chemotherapeutic agents described above.

"Active" or "activity" for the purposes herein refers to form(s) of IFN-ε or to other polypeptides (e.g. antibodies) or organic or inorganic small molecules, peptides, etc. which retain the biological and/or immunological activities/ properties of a native or naturally-occurring IFN-ε which retain the biologic and/or immunologic activities of native or naturally-occurring IFN-ε. A preferred biological activity is the ability to activate components of the JAC-STAT signaling pathway, and typical activities include, but are not limited to, antiviral, immunoregulatory or antiproliferative properties.

"Biological activity" in the context of an antibody or another molecule that can be identified by the screening assays disclosed herein (e.g. an organic or inorganic small molecule, peptide, etc.) is used to refer to the ability of such molecules to invoke one or more of the effects listed hereinabove in connection with the definition of a "therapeutically effective amount." In a specific embodiment, "biological activity" is the ability to inhibit neoplastic cell growth or proliferation. A preferred biological activity is inhibition, including slowing or complete stopping, of the growth of a target tumor (e.g. cancer) cell. Another preferred biological activity is cytotoxic activity resulting in the death of the target tumor (e.g. cancer) cell. Yet another preferred biological activity is the induction of apoptosis of a target tumor (e.g. cancer) cell. In a still further embodiment "biological activity" is an antiviral or immunoregulatory activity.

The phrase "immunological property" means immunological cross-reactivity with at least one epitope of an IFN-ε polypeptide.

"Immunological cross-reactivity" as used herein means that the candidate polypeptide is capable of competitively inhibiting the qualitative biological activity of an IFN-ε polypeptide having this activity with polyclonal antisera raised against the known active IFN-ε polypeptide. Such antisera are prepared in conventional fashion by injecting goats or rabbits, for example, subcutaneously with the known active analogue in complete Freund's adjuvant, followed by booster intraperitoneal or subcutaneous injection in incomplete Freunds. The immunological cross-reactivity preferably is "specific", which means that the binding affinity of the immunologically cross-reactive molecule (e.g. antibody) identified, to the IFN-ε polypeptide is significantly higher (preferably at least about 2-times, more preferably at least about 4-times, even more preferably at least about 6-times, most preferably at least about 8-times higher) than the binding affinity of that molecule to any other known native polypeptide.

The term "antagonist" is used in the broadest sense, and includes any molecule that partially or fully blocks, inhibits, or neutralizes a biological activity of a native IFN-ε polypeptide disclosed herein. In a similar manner, the term "agonist" is used in the broadest sense and includes any molecule that mimics a biological activity of a native IFN-ε polypeptide disclosed herein.

A "small molecule" is defined herein to have a molecular weight below about 500 daltons.

The term "antibody" is used in the broadest sense and specifically covers single anti-IFN-ε monoclonal antibodies (including agonist, antagonist, and neutralizing antibodies) and anti-IFN-ε antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *NIH Publ. No. 91–3242*, Vol. I, pages 647–669 (1991)). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" to "CDR" (i.e. residues 24–34 (L1), 50–56 (L2) and 89–97 (L3) in the light chain variable domain and 31–15 (H1), 50–65 (H2) and 95–102 (H3) in the heavy chain variable domain; Kabat et al., *Sequences of Proteins of Immunological Interest*, 5th Ed. Public Health Service, National Institute of Health, Bethesda, Md. [1991]) and/or those residues from a "hypervariable loop" (i.e. residues 26–32 (L1), 50–52 (L2) and 91–96 (L3) in the light chain variable domain and 26–32 (H1) 53–55 (H2) and 96–101 (H3) in the heavy chain variable domain; Clothia and Lesk, *J. Mol. Biol.* 196:901–917 [1987]). "Framework" or "FR" residues are those variable domain residues other than the hypervariable region residues as herein defined.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10) :1057–1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (η) and lambda (λ), based on the amino acid sequences of their constant domains.

Depending on the amino acid sequence of the constant domain of their heavy chains, inimunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 [1975], or may be made by recombinant DNA methods (see, e.g., U.S. Pat. No. 4,816,567). The "monoclonal antibodies" may also be isolated from phage antibody libraries using the techniques described in Clackson et al., Nature, 352:624–628 [1991] and Marks et al., J. Mol. Biol., 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851–6855 [1984]).

"Humanized" forms of non-human (e.g., murine) antibodies are chimeric immunoglobulins immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321:522–525 (1986); Reichmann et al., Nature, 332:323–329 [1988]; and Presta, Curr. Op. Struct. Biol., 2:593–596 (1992). The humanized antibody includes a PRIMATIZED™ antibody wherein the antigen-binding region of the antibody is derived from an antibody produced by immunizing macaque monkeys with the antigen of interest.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds., Springer-Verlag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161: and Hollinger et al., Proc. Natl. Acad. Sci. USA, 90:6444–6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO211, PRO228, PRO538, PRO172, or PRO182 polypeptide or an antibody thereto and, optionally, a chemotherapeutic agent) to a mammal. The components of the liposome are commonly is arranged in a bilayer formation, similar to the lipid arrangement of biological membranes.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any imnimunoglobulin, such as IgG-1, IgG-2, IgG-3, or IgG-4 subtypes, IgA (including IgA-1 and IgA-2), IgE, IgD or IgM.

2. Compositions and Methods of the Invention a. Full-Length human IFN-ε polypeptide The present invention provides newly identified and isolated nucleotide sequences encoding novel human interferon polypeptides originally referred to as PRO655, and now renamed as "IFN-ε". In particular, Applicants have identified and isolated cDNA encoding a novel polypeptide, as disclosed in further detail in the Examples below. Using BLAST and FastA sequence alignment computer programs, Applicants found that a full-length native sequence PRO655 polypeptide (shown in FIG. 1 and SEQ ID NO:1) has about 35–40% amino acid sequence identity with the sequence of various human IFN-α species. Specifically, the sequence identity is about 33% and 37% to IFN-α2 and IFN-β, respectively. The sequence identity with IFN-α14 is 38%. The homology is highest within the 22–189 amino acid region of the sequence of FIG. 1 (SEQ ID NO:1). At the nucleotide level, the sequence identity with the coding sequence of IFN-α is about 60%. Accordingly, we have concluded that PRO655 is a newly identified, novel member of the human interferon family which may possess antiviral, immunoregulatory and/or antiproliferative activities typical of the human interferon family. The relationship of this distinct, novel human interferon to some known IFN-α species and IFN-β is illustrated in FIGS. 5 and 7.

b. IFN-ε Variants

In addition to the full-length native sequence IFN-ε described herein, it is contemplated that IFN-ε variants can be prepared. IFN-ε variants can be prepared by introducing appropriate nucleotide changes into the DNA encoding IFN-ε, or by synthesis of the desired polypeptide. Those skilled in the art will appreciate that amino acid changes may alter post-translational processes of the IFN-ε, such as changing the number or position of glycosylation sites or altering the membrane anchoring characteristics.

It is well known that interferons tend to oligomerize. Although the etiology of these oligomers is not entire understood, it is believed, that certain oligomeric forms result from two or more interferon molecules becoming irreversibly associated with one another through intermolecular covalent bonding, such as by disulfide linkages. This problems has been observed particularly with respect to leukocyte and fibroblast interferons. (See, e.g. U.S. Pat. No. 4,816,566) Accordingly, it may be desirable to prepare amino acid variants of the native IFN-ε polypeptides of the present invention in which one or more cysteine residues are deleted or substituted by residues of other amino acids which are incapable of disulfide bond formation. Preferred variants substantially retain, mimic or antagonize the biological activity of the IFN-ε from which they are derived. As noted before, the native IFN-ε sequence includes cysteine residues at positions 53, 163 and 175 in the sequence of FIG. 1 (SEQ ID NO:1). In a preferred embodiment, at least one of the cysteine residues at positions 53, 163, and 175 is replaced by amino acid residues that are incapable of forming intermolecular disulfide bonds.

Variations in the native full-length sequence IFN-ε or in various domains of the IFN-ε described herein, can be made, for example, using any of the techniques and guidelines for conservative and non-conservative mutations set forth, for instance, in U.S. Pat. No. 5,364,934. Variations may be a substitution, deletion or insertion of one or more codons encoding IFN-ε that results in a change in the amino acid sequence of IFN-ε as compared with the native sequence IFN-ε. Optionally the variation is by substitution of at least one amino acid with any other amino acid in one or more of the domains of IFN-ε. Guidance in determining which amino acid residue may be inserted, substituted or deleted without adversely affecting the desired activity may be found by comparing the sequence of IFN-ε with that of homologous known protein molecules and minimizing the number of amino acid sequence changes made in regions of high homology. Amino acid substitutions can be the result of replacing one amino acid with another amino acid having similar structural and/or chemical properties such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay described in the Examples below.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Giene*, 34:315 (1985)], restriction selection mutagenesis [Wells et al., *Philos. Trans. R. Soc. London SerA*, 317:415 (1986)] or other known techniques can be performed on the cloned DNA to produce the IFN-ε variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isomeric amino acid can be used.

c. Modifications of IFN-ε

Covalent modifications of IFN-ε are included within the scope of this invention. One type of covalent modification includes reacting targeted amino acid residues of the IFN-ε polypeptide with an organic derivatizing agent that is capable of reacting with selected side chains or the N- or C-terminal residues of IFN-ε. Derivatization with bifunctional agents is useful, for instance, for crosslinking IFN-ε to a water-insoluble support matrix or surface for use in the method for purifying anti-IFN-ε antibodies, and vice-versa. Commonly used crosslinking agents include e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of the IFN-ε polypeptide included within the scope of this invention comprises altering the native glycosylation pattern of the polypeptide. "Altering the native glycosylation pattern" is intended for purposes herein to mean deleting one or more carbohydrate moieties found in native sequence IFN-ε, and/or adding one or more glycosylation sites that are not present in the native sequence IFN-ε, and/or altering the nature (profile) of the sugar moieties attached to the polypeptide at various glycosylation sites.

Addition of glycosylation sites to the IFN-ε polypeptide may be accomplished by altering the amino acid sequence. The alteration may be made, for example, by the addition of, or substitution by, one or more serine or threonine residues to the native sequence IFN-ε (for O-linked glycosylation sites). The IFN-ε amino acid sequence may optionally be altered through changes at the DNA level, particularly by mutating the DNA encoding the IFN-ε polypeptide at preselected bases such that codons are generated that will translate into the desired amino acids.

Another means of increasing the number of carbohydrate moieties on the IFN-ε polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the IFN-ε polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of IFN-ε comprises linking the IFN-ε polypeptide to one of a variety of non-proteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337. For example, PEGylated variants are expected to have a longer half-life and/or shorter clearance than the corresponding, non-PEGylated IFN-ε polypeptide.

The IFN-ε molecules of the present invention may also be modified in a way to form a chimeric molecule comprising IFN-ε fused to another, heterologous polypeptide or amino acid sequence. In one embodiment, such a chimeric molecule comprises a fusion of the IFN-ε with a tag polypeptide which provides an epitope to which an anti-tag antibody can selectively bind. The epitope tag is generally placed at the amino- or carboxyl-terminus of the IFN-ε. The presence of such epitope-tagged forms of the IFN-ε can be detected using an antibody against the tag polypeptide. Also, provision of the epitope tag enables the IFN-ε to be readily purified by affinity purification using an anti-tag antibody or another type of affinity matrix that binds to the epitope tag.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

In another embodiment, the chimeric molecule may comprise a fusion of the IFN-ε with an immunoglobulin or a particular region of an immunoglobulin. For a bivalent form of the chimeric molecule, such a fusion could be to the Fc region of an IgG molecule, to form an "immnunoadhesin" as hereinbefore defined. The fusion is preferably to a heavy chain constant region sequence, e.g., a hinge, CH2 and CH3 regions, or the CH1, hinge, CH2 and CH3 regions of an IgG immunoglobulin. Immunoadhesins are expected to have a longer half-life and/or slower clearance than the corresponding IFN-ε polypeptide.

d. Preparation of IFN-ε

The description below relates primarily to production of IFN-ε by culturing cells transformed or transfected with a vector containing nucleic acid encoding IFN-ε. It is, of course, contemplated that alternative methods, which are well known in the art, may be employed to prepare IFN-ε. For instance, the IFN-ε sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149–2154 (1963)]. In vitrio protein synthesis may be performed using manual techniques or by automation. Automated synthesis may be accomplished, for instance, using an Applied Biosystems Peptide Synthesizer (Foster City, Calif.) using manufacturer's instructions. Various portions of IFN-ε may be chemically synthesized separately and combined using chemical or enzymatic methods to produce the full-length IFN-ε.

i. Isolation of DNA Encoding IFN-ε

DNA encoding IFN-ε may be obtained from a cDNA library prepared from tissue believed to possess the IFN-ε mRNA and to express it at a detectable level. Accordingly, human IFN-ε DNA can be conveniently obtained from a cDNA library prepared from human tissue, such as described in the Examples. The IFN-ε-encoding gene may also be obtained from a genomic library or by oligonucleotide synthesis.

Libraries can be screened with probes (such as antibodies to IFN-ε or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding IFN-ε is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, usingy conventional primer extension procedures as described in Sambrook et al., supra, to detect precursors and processing intermediates of mRNA that may not have been reverse-transcribed into cDNA.

ii. Selection and Transformation of Host Cells

Host cells are transfected or transformed with expression or cloning vectors described herein for IFN-ε production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler. ed. (IRL Press, 1991) and Sambrook et al., supra.

Methods of transfection are known to the ordinarily skilled artisan, for example, CaPO$_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., Gene, 23:315 (1983) and WO 89/05859 published Jun. 29, 1989. For mammalian cells without such cell walls, the calcium phosphate precipitation method of Graham and van der Eb, *Virology*, 52:456–457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to Eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for IFN-ε-encoding vectors. *Saccharomyces cerevisiae* is a commonly used lower eukaryotic host microorganism.

Suitable host cells for the expression of glycosylated IFN-ε are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651): human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, Biol. Reprod., 23 243–251 (1980)); human lung cells (W138, ATCC CCL, 75); human liver cells (Hep G2, HB 8065); and mouse mammary tumor (MMT 060562, ATCC CCL51). The selection of the appropriate host cell is deemed to be within the skill in the art.

iii. Selection and Use of a Replicable Vector

The nucleic acid (e.g., cDNA or genomic DNA) encoding IFN-ε may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

IFN-ε may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the IFN-ε-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharoimyces and Kluyveroimyces α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins e.g., ampicillin, neomycin, methotrexate, or tetracycline, (b) complement auxotrophic deficiencies, or ĉ supply critical nutrients not available from complex media, e.g., the gene encoding D-alanine racemase for Bacilli.

An example of suitable selectable markers for mammalian cells are those that enable the identification of cells competent to take up the PRO655 nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979), Kingsman et al., *Gene*, 7:141 (1979); Tschemper et al., *Gene*, 10:157 (1980)]. The trp 1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the nucleic acid sequence encoding IFN-ε to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978): Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21–25 (1983)]. Promoters for use in bacterial systems also will contain a Shine-Dalgarno (S.D.) sequence operably linked to the DNA encoding IFN-ε.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomcrase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

IFN-ε transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the IFN-ε by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the IFN-ε coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding IFN-ε.

Still other methods, vectors, and host cells suitable for adaptation to the synthesis of IFN-ε in recombinant vertebrate cell culture are described in Gething et al., *Nature*, 293:620–625 (1981); Mantei et al., *Nature*, 281:40–46 (1979); EP 117,060; and EP 117,058.

iv. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*. 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes. RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence IFN-ε polypeptide or against a synthetic peptide based on the DNA sequences provided herein or against exogenous sequence fused to IFN-ε DNA and encoding a specific antibody epitope.

v. Purification of IFN-ε Polypeptide

Forms of IFN-ε may be recovered from culture medium or from host cell lysates. If membrane-bound, it can be released from the membrane using a suitable detergent solution (e.g. Triton-X 100) or by enzymatic cleavage. Cells employed in expression of IFN-ε can be disrupted by various physical or chemical means, such as freeze-thaw cycling, sonication, mechanical disruption, or cell lysing agents.

It may be desired to purify IFN-ε from recombinant cell proteins or polypeptides. The following procedures are exemplary of suitable purification procedures: by fractionation on an ion-exchange column; ethanol precipitation, reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the IFN-ε. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular IFN-ε produced.

e. Uses for IFN-ε

Nucleotide sequences (or their complement) encoding IFN-ε have various applications in the art of molecular biology, including uses as hybridization probes, in chromosome and gene mapping and in the generation of anti-sense RNA and DNA. IFN-ε encoding nucleic acid will also be useful for the preparation of IFN-ε polypeptides by the recombinant techniques described herein.

The full-length native sequence gene encoding IFN-ε (DNA50960, FIG. 2, SEQ ID NO:2), or portions thereof, may be used as hybridization probes for a cDNA library to isolate the full-length gene or to isolate still other genes (for instance, those encoding naturally-occurring variants of IFN-ε or IFN-ε from other species) which have a desired sequence identity to the IFN-ε sequence disclosed in FIG. 2 (SEQ ID NO:2). Optionally, the length of the probes will be about 20 to about 50 bases. The hybridization probes may be derived from the nucleotide sequence of SEQ ID NO:2 or from genomic sequences including promoters. enhancer elements and introns of native sequence IFN-ε. By way of example, a screening method will comprise isolating the coding region of the IFN-ε gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the IFN-ε gene of the present invention can be used to screen libraries of human cDNA, genomic DNA or mRNA to determine which members of such libraries the probe hybridizes to. Hybridization techniques are described in further detail in the Examples below.

The probes may also be employed in PCR techniques to generate a pool of sequences for identification of closely related IFN-ε sequences.

Nucleotide sequences encoding an IFN-ε polypeptide can also be used to construct hybridization probes for mapping the gene which encodes that IFN-ε and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries. Other interferons, e.g. IFNs-α1, α8, α10, α14, α16, α21, β1, and omega1 have been mapped to Chromosome 9.

The novel human interferon-ε (PRO655) can also be used in assays to identify and purify its receptor, and to identify other proteins or molecules involved in the ligand/receptor binding interaction. By such methods, inhibitors of the receptor/ligand binding interaction can be identified. Proteins involved in such binding interactions can also be used to screen for peptide or small molecule inhibitors or agonists of the binding interaction. Screening assays can be designed to find lead compounds that mimic the biological activity of a native PRO655 interferon or a receptor for PRO655. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode IFN-ε (PRO655) or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding IFN-ε (PRO655) can be used to clone genomic DNA encoding PRO655 in accordance with established techniques and the genomic sequences used to generate transgenic animals that contain cells which express DNA encoding PRO655. Methods for generating transgenic animals, particularly animals such as mice or rats, have become conventional in the art and are described, for example, in U.S. Pat. Nos. 4,736,866 and 4,870,009. Typically, particular cells would be targeted for IFN-ε transgene incorporation with tissue-specific enhancers. Transgenic animals that include a copy of a transgene encoding IFN-ε introduced into the germ line of the animal at an embryonic stage can be used to examine the effect of increased expression of DNA encoding IFN-ε. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of IFN-ε (PRO655) can be used to construct a IFN-ε "knock out" animal which has a defective or altered gene encoding IFN-ε as a result of homologous recombination between the endogenous gene encoding IFN-ε and altered genomic DNA encoding IFN-ε introduced into an embryonic cell of the animal. For example, cDNA encoding IFN-ε can be used to clone genomic DNA encoding IFN-ε in accordance with established techniques. A portion of the genomic DNA encoding IFN-ε can be deleted or replaced with another gene. such as a gene encoding a selectable marker which can be used to monitor integration. Typically, several kilobases of unaltered flanking DNA (both at the 5' and 3' ends) are included in the vector [see e.g., Thomas and Capecchi. *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the IFN-ε (PRO655) polypeptide.

The novel IFN-ε (PRO655) human interferon polypeptides of the present invention have antiviral, antiproliferative and/or immunoregulatory activities. Thus, IFN-ε, including variants and derivatives of the native protein, may be used for the treatment of malignant or non-malignant conditions associated with unwanted cell proliferation, or viral diseases. More particularly, IFN-ε may be useful for the treatment of diseases characterized by tumorigenic or neoplastic cell growth, malignant hematological systemic diseases, viral disease, asthma, carcinomas, sarcomas, myelomas, melanomas, lymphomas, papillomas, degenerative diseases, allergic diseases psoriasis and pain. Dosages can be calculated based upon the specific activity of IFN-ε as compared to the specific activities of other, known interferons, which have been used to treat similar conditions.

The IFN-ε polypeptides and their agonists may also be used as adjuncts to chemotherapy. It is well understood that chemotherapeutic treatment results in suppression of the immune system. Often, although successful in destroying the tumor cells against which they are directed, chemotherapeutic treatments result in the death of the subject due to such side effects of the chemotherapeutic agents. Administration of the IFN-ε polypeptides or their agonists may prevent this side effect as a result of their ability to upregulate the subject's immune system. In general, patients suffering from immunesuppression due to any underlying cause, including HIV infection (or AIDS), may benefit from treatment with the IFN-ε polypeptides or agonist thereof.

f. Anti-IFN-ε Antibodies

The present invention further provides anti-IFN-ε antibodies. Exemplary antibodies include polyclonal, monoclonal, humanized, bispecific, and heteroconjugate antibodies.

i. Polyclonal Antibodies

The anti-IFN-ε antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the IFN-ε polypeptide or a fusion protein thereof. It may be useful to conjugate the immunizing agent to a protein known to be immunogenic in the mammal being inmmunized. Examples of such imrnunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

ii. Monoclonal Antibodies

The anti-IFN-ε antibodies may, alternatively, be monoclonal antibodies. Monoclonal antibodies may be prepared using hybridoma methods, such as those described by Kohier and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the anti-IFN-ε polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif., and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against anti-IFN-ε. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently oining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

iii. Humanized and Human Antibodies

The anti-IFN-ε antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., J. Mol. Biol., 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)].

iv. Bispecific Antibodies

Bispecific antibodies are monoclonal, preferably human or humanized, antibodies that have binding specificities for at least two different antigens. In the present case, one of the binding specificities is for the IFN-ε, the other one is for any other antigen, and preferably for a cell-surface protein or receptor or receptor subunit. In a further embodiment, one specificity is for IFN-ε, while the other specificity is for type I interferon, preferably IFN-α.

Methods for making bispecific antibodies are known in the art. Traditionally, the recombinant production of bispecific antibodies is based on the co-expression of two immnunoglobulin heavy-chain/light-chain pairs, where the two heavy chains have different specificities [Milstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

v. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, imnmunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med*. 176:1191–1195 (1992) and Shopes, B. *J. Immunol*. 148:2918–2922 (1992). Homodimeric antibodies with enhanced anti-tumor activity may also be prepared using heterobifunctional cross-linkers as described in Wolff et al. *Cancer Research* 53 :2560–2565 (1993). Alternatively, an antibody can be engineered which has dual Fc regions and may thereby have enhanced complement lysis and ADCC capabilities. See Stevenson et al., *Anti-Cancer Drug Design* 3:219–230 (1989).

7. Immunoconjugates

The invention also pertains to immunoconjugates comprising an antibody conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

8. Immunoliposomes

The antibodies disclosed herein may also be forrmulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl Acad. Sci. USA*, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem*. 257: 286–288 (1982) via a disulfide interchange reaction. A chemotherapeutic agent (such as Doxorubicin) is optionally contained within the liposome. See Gabizon et al., *J. National Cancer Inst*. 81(19)1484 (1989).

g. Uses for anti-IFN-ε Antibodies

The anti-IFN-ε antibodies of the invention have various utilities. For example, anti-IFN-ε antibodies may be used in diagnostic assays for IFN-ε, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For examnple, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-IFN-ε antibodies also are useful for the affinity purification of IFN-ε from recombinant cell culture or natural sources. In this process, the antibodies against IFN-ε are immobilized on a suitable support, such a Sephadex resin or filter paper, using methods well known in the art. The immobilized antibody then is contacted with a sample containing the IFN-ε to be purified, and thereafter the support is washed with a suitable solvent that will remove substantially all the material in the sample except the IFN-ε, which is bound to the immobilized antibody. Finally, the support is washed with another suitable solvent that will release the IFN-ε from the antibody.

Agonist antibodies specifically binding IFN-ε mimic its biological activities and thus are potentially useful for the treatment of the same or similar conditions as those targeted by IFN-ε itself. Such conditions include, for example, neoplastic cell growth, e.g. tumor (including cancer), viral infections, autoimmune diseases and, in general, conditions where the upregulation of the immune system is desirable.

Antagonist antibodies specifically binding IFN-ε may be used to treat conditions associated with the overexpression of IFN-ε. Such conditions might include various autoimmune diseases, such as systemic lupus erythematoses, Behcet's disease, and insulin-dependent diabetes mellitus (IDDM, also referred to as type I diabetes).

H. Animal Models for Testing Anti-Tumor Activity

A variety of well known animal models can be used to further understand the role of IFN-ε in the development and pathogenesis of tumors, and to test the efficacy of candidate therapeutic agents, including antibodies, and other agonists of the native polypeptide, including small molecule agonists. The in vivo nature of such models makes them particularly predictive of responses in human patients. Animal models of tumors and cancers (e.g. breast cancer, colon cancer, prostate cancer, lung cancer, etc.) include both non-recombinant and recombinant (transgenic) animals. Non-recombinant animal models include, for example, rodent, e.g., murine models. Such models can be generated by introducing tumor cells into syngeneic mice using standard techniques, e.g. subcutaneous injection, tail vein injection, spleen implantation, intraperitoneal implantation, implantation under the renal capsule, or orthopin implantation, e.g. colon cancer cells implanted in colonic tissue. (See, e.g. PCT publication No. WO 97/33551, published Sep. 18, 1997).

Probably the most often used animal species in oncological studies are immunodeficient mice and, in particular, nude mice. The observation that the nude mouse with hypo/aplasia could successfully act as a host for human tumor xenografts has lead to its widespread use for this purpose. The autosomal recessive nu gene has been introduced into a very large number of distinct congenic strains of nude mouse, including, for example, ASW, A/He, AKR, BALB/c, B10.LP, C17, C3H, C57BL, C57, CBA, DBA, DDD, I/st, NC, NFR, NFS, NFS/N, NZB, NZC, NZW, P, RIII and SJL. In addition, a wide variety of other animals with inherited immunological defects other than the nude mouse have been bred and used as recipients of tumor xenografts. For further details see, e.g. *The Nude Mouse in Oncology Research*, E. Boven and B. Winograd, eds., CRC Press, Inc., 1991.

The cells introduced into such animals can be derived from known tumor/cancer cell lines, such as, any of the above-listed tumor cell lines, and, for example, the B104-1-1 cell line (stable NIH-3T3 cell line transfected with the neu protooncogene); ras-transfected NIH-3T3 cells; Caco-2 (ATCC HTB-37); a moderately well-differentiated grade II human colon adenocarcinoma cell line, HT-29 (ATCC HTB-38), or from tumors and cancers. Samples of tumor or cancer cells can be obtained from patients undergoing surgery, using standard conditions, involving freezing and storing in liquid nitrogen (Karmali et al., *Br. J. Cancer* 48, 689–696 [1983]).

Tumor cells can be introduced into animals, such as nude mice, by a variety of procedures. The subcutaneous (s.c.) space in mice is very suitable for tumor implantation. Tumors can be transplanted s.c. as solid blocks, as needle biopsies by use of a trochar, or as cell suspensions. For solid block or trochar implantation, tumor tissue fragments of suitable size are introduced into the s.c. space. Cell suspensions are freshly prepared from primary tumors or stable tumor cell lines, and injected subcutaneously. Tumor cells can also be injected as subdermal implants. In this location, the inoculum is deposited between the lower part of the dermal connective tissue and the s.c. tissue. Boven and Winograd (1991), supra.

Animal models of breast cancer can be generated, for example, by implanting rat neuroblastoma cells (from which the neu oncogen was initially isolated), or neu-transformed NIH-3T3 cells into nude mice, essentially as described by Drebin et al. *PNAS USA* 83, 9129–9133 (1986).

Similarly, animal models of colon cancer can be generated by passaging colon cancer cells in animals, e.g. nude mice, leading to the appearance of tumors in these animals. An orthotopic transplant model of human colon cancer in nude mice has been described, for example, by Wang et al., *Cancer Research* 54, 4726–4728 (1994) and Too et al., *Cancer Research* 55, 681–684 (1995). This model is based on the so-called "METAMOUSE" sold by AntiCancer, Inc. (San Diego. Calif.).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines.

For example, Meth A, CMS4, CMS5, CMS21, and WEHI-164 are chemically induced fibrosarcomas of BALB/c female mice (DeLeo et al., *J. Exp. Med.* 146, 720 [1977]), which provide a highly controllable model system for studying the anti-tumor activities of various agents (Palladino et al., *J. Immunol.* 138, 4023–4032 [1987]). Briefly, tumor cells are propagated in vitro in cell culture. Prior to injection into the animals, the cell lines are washed and suspended in buffer, at a cell density of about $10 \times 10^6$ to $10 \times 10^7$ cells/ml. The animals are then infected subcutaneously with 10 to 100 μl of the cell suspension allowing one to three weeks for a tumor to appear.

In addition, the Lewis lung (3LL) carcinoma of mice, which is one of the most thoroughly studied experimental tumors, can be used as an investigational tumor model. Efficacy in this tumor model has been correlated with beneficial effects in the treatment of human patients diagnosed with small cell carcinoma of the lung (SCCL). This tumor can be introduced in normal mice upon injection of tumor fragments from an affected mouse or of cells maintained in culture (Zupi et al., *Br. J. Cancer* 41, suppl. 4, 309 [1980]), and evidence indicates that tumors can be started from injection of even a single cell and that a very high proportion of infected tumor cells survive. For further information about this tumor model see Zacharski, *Haemostasis* 16, 300–320 [1986]).

One way of evaluating the efficacy of a test compound in an animal model is implanted tumor is to measure the size of the tumor before and after treatment. Traditionally, the size of implanted tumors has been measured with a slide caliper in two or three dimensions. The measure limited to two dimensions does not accurately reflect the size of the tumor, therefore, it is usually converted into the corresponding volume by using a mathematical formula. However, the measurement of tumor size is very inaccurate. The therapeutic effects of a drug candidate can be better described as treatment-induced growth delay and specific growth delay. Another important variable in the description of tumor growth is the tumor volume doubling time. Computer programs for the calculation and description of tumor growth are also available, such as the program reported by Rygaard and Spang-Thomsen, *Proc. 6th Int. Workshop on Immune-Deficieni Animals*, Wu and Sheng eds., Basel, 1989, 301. It is noted, however, that necrosis and inflammatory responses following treatment may actually result in an increase in tumor size, at least initially. Therefore, these changes need to be carefully monitored, by a combination of a morphometric method and flow cytometric analysis.

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA* 82, 6148–615 [1985]); gene targeting in embryonic stem cells (Thompson et al., *Cell* 56, 313–321 [1989]); electroporation of embryos (Lo, *Mol. Cel. Biol.* 3, 1803–1814 [1983]); sperm-mediated gene transfer (Lavitrano et al., *Cell* 57, 717–73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA* 89, 6232–636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. The animals are further examined for signs of tumor or cancer development.

The efficacy of IFN-ε, antibodies specifically binding IFN-ε and other drug candidates, can be tested also in the treatment of spontaneous animal tumors. A suitable target for such studies is the feline oral squamous cell carcinoma (SCC). Feline oral SCC is a highly invasive, malignant tumor that is the most common oral malignancy of cats, accounting for over 60% of the oral tumors reported in this species. It rarely metastasizes to distant sites, although this low incidence of metastasis may merely be a reflection of the short survival times for cats with this tumor. These tumors are usually not amenable to surgery, primarily because of the anatomy of the feline oral cavity. At present, there is no effective treatment for this tumor. Prior to entry into the study, each cat undergoes complete clinical examination, biopsy, and is scanned by computed tomography (CT). Cats diagnosed with sublingual oral squamous cell tumors are excluded from the study. The tongue can become paralyzed as a result of such tumor, and even if the treatment kills the tumor, the animals may not be able to feed themselves. Each cat is treated repeatedly, over a longer period of time. Photographs of the tumors will be taken daily during the treatment period, and at each subsequent recheck. After treatment, each cat undergoes another CT scan. CT scans and thoracic radiograms are evaluated every 8 weeks thereafter. The data are evaluated for differences in survival, response and toxicity as compared to control groups. Positive response may require evidence of tumor regression, preferably with improvement of quality of life and/or increased life span.

In addition, other spontaneous animal tumors, such as fibrosarcoma, adenocarcinoma, lymphoma, chrondroma, leiomyosarcoma of dogs, cats, and baboons can also be tested. Of these mammary adenocarcinoma in dogs and cats is a preferred model as its appearance and behavior are very similar to those in humans. However, the use of this model is limited by the rare occurrence of this type of tumor in animals.

I. Screening Assays for Drug Candidates

Screening assays for drug candidates are designed to identify compounds that competitively bind or complex with the receptor(s) of IFN-ε, and signal through such receptor(s) (e.g. IFN-αR, including both subunits, and any other receptor that might be identified hereinafter as being involved in IFN-ε signal transduction). Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art.

In binding assays, the interaction is binding and the complex formed can be isolated or detected in the reaction mixture. In a particular embodiment, a receptor of a polypeptide encoded by the gene identified herein or the drug candidate is immobilized on a solid phase, e.g. on a microtiter plate, by covalent or non-covalent attachments. Non-covalent attachment generally is accomplished by coating the solid surface with a solution of the polypeptide and drying. Alternatively, an immobilized antibody, e.g. a monoclonal antibody, specific for the polypeptide to be immobilized can be used to anchor it to a solid surface. The assay is performed by adding the non-immobilized component, which may be labeled by a detectable label, to the immobilized component, e.g. the coated surface containing the anchored component. When the reaction is complete, the non-reacted components are removed e.g. by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to the IFN-ε receptor, its interaction with the receptor can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, Nature (London) 340, 245–246 (1989); Chien et al., *Proc. Natl. Acad. Sci. USA* 88, 9578–9582 (1991)] as disclosed by Chevray and Nathans [*Proc. Natl. Acad. Sci. USA* 89, 5789–5793 (1991)]. Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Methods to screen potential agents for their ability to inhibit neoplastic cell growth can be designed without detailed knowledge of the precise mechanism, although the knowledge of such mechanism may certainly be helpful. For example, after it has been determined that neoplastic cell growth (e.g. tumor growth) is correlated wit subnormal expression (or activity) of a gene identified herein, agents can be screened for their ability to increase such gene expression and/or restore normal activity.

J. Pharmaceutical Compositions

The IFN-ε polypeptides of the present invention, agonist antibodies specifically binding such polypeptides, as well as other molecules identified by the screening assays disclosed hereinbefore, can be administered for the treatment of various pathologic conditions discussed hereinabove, such as. tumors, including cancers, viral diseases, and as immunomodulatory agents, in the form of pharmaceutical compositions.

Therapeutic formulations of the IFN-ε polypeptides identified herein, or agonists thereof are prepared for storage by mixing the active ingredient having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkoniwm chloride, benzethonium chloride; phenol, butyl or benzyl alcohol, alkyl parabens such as methyl or propyl paraben; catechol; resorcinol, cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmnaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-metliacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT ™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Where antibody fragments are used, the smallest inhibitory fragment which specifically binds to the binding domain of the target protein is usually preferred. For example, based upon the variable region sequences of an antibody, peptide molecules can be designed which retain the ability to bind the target protein sequence. Such peptides can be synthesized chemically and/or produced by recombinant DNA technology (see. e.g. Marasco et al., *Proc. Natl. Acad. Sci. USA* 90, 7889–7893 [1993]). It is noted, however, that for some purposes, such as, to determine the pK value, a larger fragment, having a longer circulatory half-life, may be preferred.

H. Methods of Treatment

It is contemplated that the IFN-ε polypeptides of the present invention and their agonists including antibodies, peptides, and small molecule agonists, may be used to treat various tumors, e.g. cancers, viral infections, and generally conditions where immunomodulation, e.g. upregulation of the immune system, is desirable.

Exemplary conditions or disorders to be treated include benign or malignant tumors (e.g. renal, liver, kidney, bladder, breast, gastric, ovarian, colorectal, prostate, pancreatic, lung, vulval, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic and immunologic disorders.

The anti-tumor agents of the present invention (including the IFN-ε polypeptides disclosed herein and agonists which mimic their activity, e.g. antibodies, peptides and small organic molecules), are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration is preferred.

Other therapeutic regimens may be combined with the administration of the anti-cancer agents of the instant invention. For example, the patient to be treated with such anti-cancer agents may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede, or follow administration of the anti-tumor agent of the present invention, or may be given simultaneously therewith. The anti-cancer agents of the present invention may be combined with an anti-oestrogen compound such as tamoxifen or an anti-progesterone such as onapristone (see, EP 616812) in dosages known for such molecules.

It may be desirable to also administer antibodies against tumor associated antigens, such as antibodies which bind to the ErbB2, EGFR, ErbB3, ErbB4, or vascular endothelial factor (VEGF). Sometimes, it may be beneficial to also administer one or more cytokines to the patient. In a preferred embodiment, the anti-cancer agents herein are co-administered with a growth inhibitory agent. For example, the growth inhibitory agent may be administered first, followed by the administration of an anti-cancer agent of the present invention. However, simultaneous administration or administration of the anti-cancer agent of the present invention first is also contemplated. Suitable dosages for the growth inhibitory agent are those presently used and may be lowered due to the combined action (synergy) of the growth inhibitory agent and the antibody herein.

For the prevention or treatment of disease, the appropriate dosage of an anti-tumor agent herein will depend on the type of disease to be treated, as defined above, the severity and course of the disease. whether the agent is administered for preventive or therapeutic purposes, previous therapy, the patient's clinical history and response to the agent, and the discretion of the attending physician. The agent is suitably administered to the patient at one time or over a series of treatments.

For example, depending on the type and severity of the disease, about 1 μg/kg to 15 mg/kg (e.g. 0.1–20mg/kg) of an antitumor agent is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

Nucleic acid encoding an IFN-ε polypeptide may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83, 4143–4146 [1986]). The oligonucleotides can be modified to enhance the uptake, e.g., by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429–4432 (1987); and Wagner et al., *Proc. Natl. Acad. Sci. USA* 87, 3410–3414 (1990).

For review of gene marking and gene therapy protocols see Anderson et al., *Science* 256, 808–813 (1992).

Techniques for reintroducing cells into a patient after engineering with a polynucleotide (RNA or DNA) encoding a polypeptide herein ex vivo (cell therapy) are well known in the art.

10. Articles of Manufacture

In another embodiment of the invention, an article of manufacture containing materials useful for the diagnosis or treatment of the disorders described above is provided.

The article of manufacture comprises a container and a label. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is an IFN-ε of the present invention, or an agonist or antagonist thereof. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

11. Diagnosis and Prognosis of Tumors

As the IFN-ε proteins disclosed herein has been found to be effective in inhibiting tumor cell proliferation or growth and/or in killing tumor cells, their reduced level of expression may be indicative of the predisposition of a patient to develop tumor, and/or of the development or progression of tumor. Accordingly antibodies directed against the proteins disclosed herein may be used as tumor diagnostics or prognostics.

For example, antibodies, including antibody fragments, can be used to qualitatively or quantitatively detect the expression of the IFN-ε protein ("marker gene product"). The antibody preferably is equipped with a detectable, e.g. fluorescent label, and binding can be monitored by light microscopy, flow cytometry, fluorimetry, or other techniques known in the art.

In situ detection of antibody binding to the marker gene product can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

In the following examples, IFN-ε is shown to be widely expressed in multiple human tissues, and to activate multiple signaling components in the JAK-STAT pathway in a IFNAR-dependent manner. The disclosed results also demonstrate that IFN-ε exhibits anti-growth and immunomodulating effects on cells. In addition, as noted before, interferons have been implicated in the pathogenesis of various autoimmune diseases, such as systemic lupus erythematoses, Behcet's disease, insulin-dependent diabetes mellitus (IDDM, also referred to as type I diabetes), and antibodies to various interferons the overexpression of which has been associated with the development and pathogenesis of such diseases have been proposed as potential therapeutics. For example, it has been demonstrated in a transgenic mouse model that β cell expression of IFN-α can cause insulitis and IDDM, and IFN-α antagonists (including antibodies) have been proposed for the treatment of IDDM (WO 93/04699, published Mar. 18, 1993). Accordingly, anti-IFN-ε antibodies might be useful in the treatment of diseases associated with the overexpression of IFN-ε.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Rockville, Md.

Example 1

Isolation of cDNA clones Encoding Human IFN-ε

An expressed sequence tag (EST) DNA database (LIFESEQ™, Incyte Pharmaceuticals, Palo Alto, Calif.) was searched and an EST was identified which showed homology to interferon-α. Possible homology was noted between Incyte EST 3728969 (subsequently renamed as DNA49668) and mammalian alpha interferons, in particular IFN-α14. The homology was confirmed by inspection.

The following PCR primers and oligonucleotide probe were synthesized:

49668.r1: TCTCTGCTTCCAGTCCCATGAGTGC (SEQ ID NO:4)

49668.r2: GCTTCCAGTCCCATGAGTGCTTCTAGG (SEQ ID NO:5)

49668.p1: GGCCATTCTCCATGAGATGCTTCAGCA-GATCTTCAGCCTCTTCAGGGCAA (SEQ ID NO:6)

In order to screen several libraries for a source of a full-length clone, DNA from the libraries was screened using the r1 and r2 probes identified above. A positive library was then used to isolate clones encoding the IFN-ε-encoding gene using the probe oligonucleotide.

Three million clones from a size selected (500–4000 bp) oligo dT primed cDNA library from human small intestine (LIB 99) constructed in a pRK5-based vector screened by hybridization. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278–1280 (1991)) in the unique XhoI and NotI sites. Only one positive clone was found out of 3.6×10⁶ cfu. The clone was sequenced in both directions and was found to cover the entire reading frame (ORF). A BAC clone (F480) was identified by screening a BAC array panel (Research Genetics) with PCR primers generated from the sequence of IFN-ε. DNA sequencing of the clone isolated as described above gave the full-length DNA sequence for DNA50960 and the derived protein sequence for IFN-ε (PRO655).

The entire nucleotide sequence of DNA50960 is shown in FIG. 2 (SEQ ID NO:2). Clone DNA50960 contains a single open reading frame with an apparent translational initiation site at nucleotide positions 621–623 (FIG. 2). The predicted polypeptide precursor is 208 amino acids long, of which 21 N-terminal amino acid residues represent a putative signal sequence. Clone DNA50960-1224 (clone F480) has been deposited with ATCC and is assigned ATCC deposit no. 209509, deposited on Dec. 3, 1997.

Figure 7A:
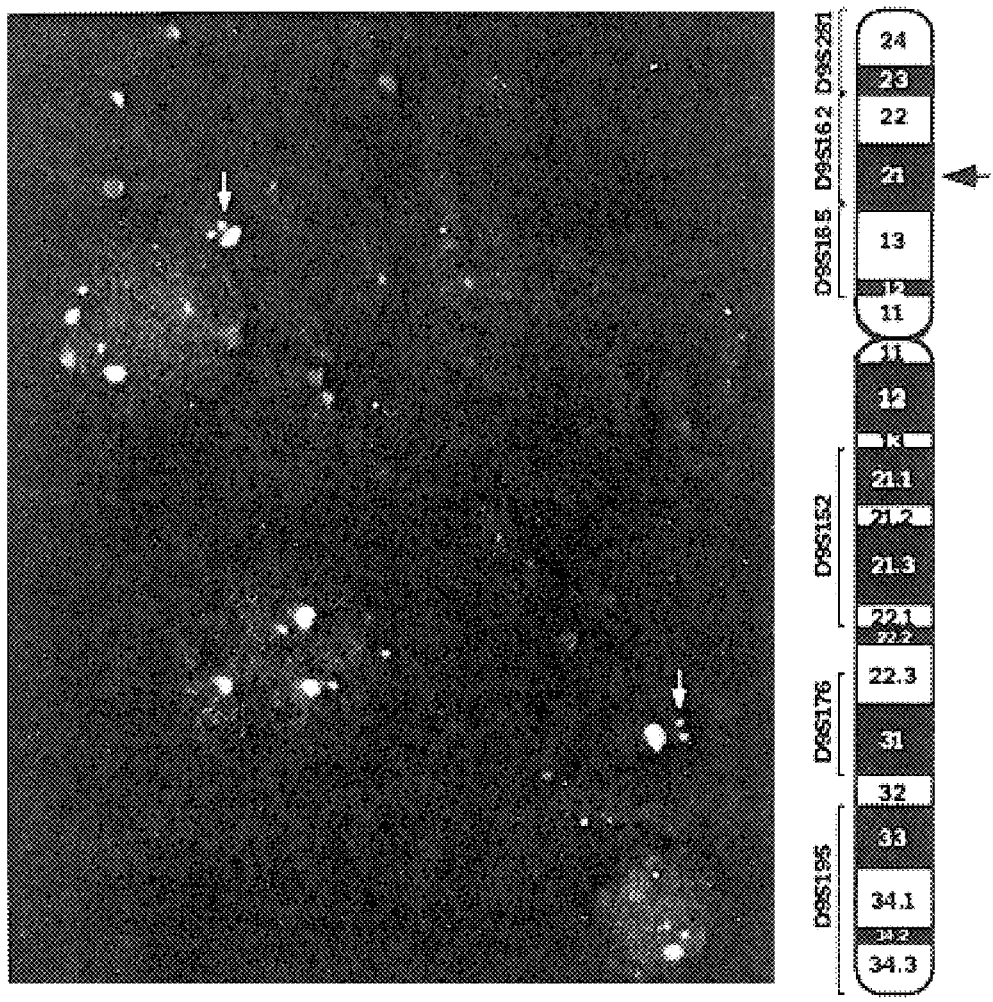
FIG. 7A shows the chromosomal localization of human IFN-ε. Human metaphasc cells were hybridized to a digoxigenin-labeled BAC clone F480 and detected by a fluoresceinated anti-digoxigenin antibody (green) and by a biotin-labeled probe specific for the heterochromatic region of chromosome 9 revealed by Texas-red avidin (red) and counterstained by DAPI. 80 metaphase cells were analyzed and 72 were specifically labeled.

Using BLAST and FastA sequence alignment computer programs, it was found that PRO655 (shown in FIG. 1 and SEQ ID NO:1) has about 35–40% amino acid sequence identity with the sequence of various human IFN-α species. The homology is highest within the 22–189 amino acid region of the sequence of FIG. 1 (SEQ ID NO:1). At the nucleotide level, the homology with the coding sequence of IFN-α is about 60%. Based upon these data as well as the presence of a characteristic sequence beginning at amino acid 147 that is typical of type I interferons ([FYH][FY]. [GNRC][LIVM].{1}[FY]L.{7}[CY]AW), this molecule was identified as a member of the type I IFN family (FIG. 7). The sequence of IFN-ε is nearly as divergent from IFN-α as it is from IFN-β family members (33% and 37% sequence identity to IFN-α$_{2a}$ and IFN-β, respectively) and thus defines a new branch on the type 1 interferon family tree. Molecular modeling suggests that IFN-ε displays similar tertiary structure compared to IFN-α (L. Presta, data not shown). A diagrammatic comparison of IFN-ε with other IFNs is shown in FIG. 7(A).

Example 2

Use of the Novel Human Interferon Encoding DNA as a Hybridization Probe

The following method describes use of a nucleotide sequence encoding IFN-ε as a hybridization probe.

DNA comprising the coding sequence of IFN-ε (as shown in FIG. 2, SEQ ID NO:2) is employed as a probe to screen for homologous DNAs (such as those encoding naturally-occurring variants of IFN-ε) in human tissue cDNA libraries or human tissue genomic libraries.

Hybridization and washing of filters containing either library DNAs is performed under the following high stringency conditions. Hybridization of radiolabeled probe derived from the PRO655-encoding DNA, to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence IFN-ε can then be identified using standard techniques known in the art.

Example 3

Expression of IFN-ε in *E. coli*

This example illustrates preparation of an unglycosylated form of IFN-ε by recombinant expression in *E. coli.*

The DNA sequence encoding IFN-ε (SEQ ID NO:2) is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*, see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the IFN-ε coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density during which the expression promoter is turned on.

After culturing the cells for several more hours, the cells can be harvested by centrifugation. The cell pellet obtained by the centrifugation can be solubilized using various agents known in the art, and the solubilized IFN-ε protein can then be purified using a metal chelating column under conditions that allow tight binding of the protein.

A specific example of the expression and purification of recombinant IFN-ε in *E coil* is provided in Example 10 below.

Example 4

Expression of IFN-ε in Mammalian Cells

This example illustrates preparation of a glycosylated form of IFN-ε (PRO655) by recombinant expression in mammalian cells.

The vector, pRK5 (see EP 307,247, published Mar. 15, 1989), is employed as the expression vector. Optionally, the IFN-ε-encoding DNA is ligated into pRK5 with selected restriction enzymes to allow insertion of the IFN-ε-encoding DNA using ligation methods such as described in Sambrook et al., supra. The resulting vector is called pRK5-IFN-ε (PRO655).

In one embodiment. the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-IFN-ε (PRO655) DNA is mixed with about 1 μg DNA encoding the VA RNA gene [Thimmappaya et al., *Cell*, 31:543 (1982)] and dissolved in 500 μl of 1 mM Tris-HCl, 0.1 mM EDTA, 0.227 M CaCl$_2$. To this mixture is added, dropwise, 500 μl of 50 mM HEPES (pH 7.35), 280 mM NaCl, 1.5 mM NaPO$_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of IFN-ε polypeptide. The cultures containing transfected cells may undergo further incubation (in serum free medium) and the medium is tested in selected bioassays.

In an alternative technique, DNA encoding IFN-ε may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-IFN-ε DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed IFN-ε can then be concentrated and purified by any selected method, such as dialysis and/or column chromatography.

In another embodiment, the novel interferon polypeptide (IFN-ε, PRO655) was transiently transfected into COS7 cells. 20 μg of a plasmid encoding IFN-ε under control of the CMV IE promoter, was mixed with 2 μg of a Green Fluorescent Protein (GFP) expressing plasmid. The DNA was introduced into the cells with a commercially available transfection reagents following manufacturer's instructions. One day post-transfection, the cells were visualized at 425 nM, using a fluorescent microscope to ensure a transfection efficiency >25% (25% GFP positive). The medium was then removed and the plates were fed 25 ml of collection media and incubated at 32° C. for 5 days. Collection media: enriched serum-free medium containing 100 ng/ml insulin. Media: high-glucose DMEM (Gibco-BRL) with 0.5% fetal bovine serum. Media were collected, cells and debris removed by centrifugation and filtration through a 0.2 μM sterile filter.

Epitope-tagged IFN-ε DNA may also be expressed in host CHO cells. The IFN-ε DNA may be subcloned out of the pRK5 vector. The subclone insert can undergo PCR to fuse in frame with a selected epitope tag such as a poly-his tag. The poly-his tagged insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged IFN-ε can then be concentrated and purified by any selected method, such as by $Ni^{2+}$-chelate affinity chromatography. Following essentially the protocol described, a poly-his tagged human IFN-ε polypeptide (PRO713) was prepared and purified. The different PRO number merely indicates that the protein was obtained in a different expression experiment. PRO713 has the same amino acid sequence as PRO655, i.e. is encoded by DNA50960.

Example 5

Expression of IFN-ε in Yeast

The following method describes recombinant expression of IFN-ε in yeast.

First, yeast expression vectors are constructed for intracellular production or secretion of IFN-ε from the ADH2/GAPDH promoter. DNA encoding IFN-ε, a selected signal peptide and the promoter is inserted into suitable restriction enzyme sites in the selected plasmid to direct intracellular expression of IFN-ε. For secretion, DNA encoding IFN-ε can be cloned into the selected plasmid, together with DNA encoding the ADH2/GAPDH promoter, the yeast alpha-factor secretory signal/leader sequence, and linker sequences (if needed) for expression of IFN-ε.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant IFN-ε can subsequently be isolated and purified by removing the yeast cells from the fermentation medium by centrifugation and then concentrating the medium using selected cartridge filters. The concentrate containing IFN-ε may further be purified using selected column chromatography resins.

Example 6

Expression of IFN-ε in Baculovirus-infected Insect Cells

The following method describes recombinant expression of IFN-ε in Baculovirus expression system.

The IFN-ε-encoding DNA is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the coding sequence of IFN-ε or the desired portion of the coding sequence is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged IFN-ε can then be purified, for example, by $Ni^{2+}$-chelate affinity chromatography as follows. Extracts are prepared from recombinant virus-infected Sf9 cells as described by Rupert et al., *Nature*, 362:175–179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation and the supernatant is diluted 50-fold in loading buffer (50 mM phosphate, 300 mM NaCl, 10% Glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the colunnn at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged IFN-ε are pooled and dialyzed against loading buffer.

Alternatively, purification of the IgG tagged (or Fc tagged) IFN-ε can be perforrned using known chromatography techniques, including for instance, Protein A or protein G column chromatography.

A specific protocol for purification of IgG-tagged proteins is as follows: The conditioned medium is filtered through a 0.45 micron filter, and loaded onto a Sepharose A column (Pharmacia). The column is washed with 5–6 CV 20 mM $NaH_2PO_4$, pH 6.8, and eluted with 3 CV 100 mM citric acid pH 3.4. After neutralization with 1 M Tris (pH 9.)) in fraction tubes (275 microliters per 1 ml fraction), the IFN-ε protein is desalted on PD-10 column.

Example 7

Preparation of Antibodies that Bind IFN-ε

This example illustrates preparation of monoclonal antibodies which can specifically bind IFN-ε.

Techniques for producing the monoclonal antibodies are known in the art and are described, for instance, in Goding, supra. Immunogens that may be employed include purified IFN-ε, fusion proteins containing IFN-ε, and cells expressing recombinant IFN-ε on the cell surface. Selection of the immunoyen can be made by the skilled artisan without undue experimentation.

Mice, such as Balb/c, are immunized with the IFN-ε immunogen emulsified in complete Freund's adjuvant and injected subcutaneously or intraperitoneally in an amount from 1–100 micrograms. Alternatively. the immunogeni is emulsified in MPL-TDM adjuvant (Ribi Immunochemical Research, Hamilton, MT) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-IFN-ε antibodies.

After a suitable antibody titer has been detected, the animals "positive" for antibodies can be injected with a final intravenous injection of IFN-ε. Three to four days later, the mice are sacrificed and the spleen cells are harvested. The spleen cells are then fused (using 35% polyethylene glycol) to a selected murine myeloma cell line such as P3X63AgU. 1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids. and spleen cell hybrids.

The hybridoma cells will be screened in an ELISA for reactivity against IFN-ε. Determination of "positive" hybridoma cells secreting the desired monoclonal antibodies against IFN-ε is within the skill in the art.

The positive hybridoma cells can be injected intraperitoneally into syngeneic Balb/c mice to produce ascites containing the anti-IFN-ε monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 8

Chromosomal Localization of IFN-ε

DNA from BAC clone F480 containing the IFN-ε gene was labeled with digoxigenin dUTP followed by standard fluorescent in situ (FISH) hybridization procedure. (Knoll and Lichter, *Current Protocols in Human Genetics*, Dracopoli et al., eds., John Wiley & Sons, New York, 1995. Units 4.3.1–4.3.29, *Current Protocols in Molecular Biology*, Ausubel et al., eds., John Wiley & Sons, New York 1997. Units 3.18; 14.7.1–14.7.14.) The initial experiment resulted in specific labeling of the short arm of a group C chromosome which was believed to be chromosome 9, based on size, morphology, and banding pattern. A second experiment was conducted in which a biotin-labeled probe which is specific for the heterochromatic region of chromosome 9 was co-hybridized with clone F480.

Figure 7B:
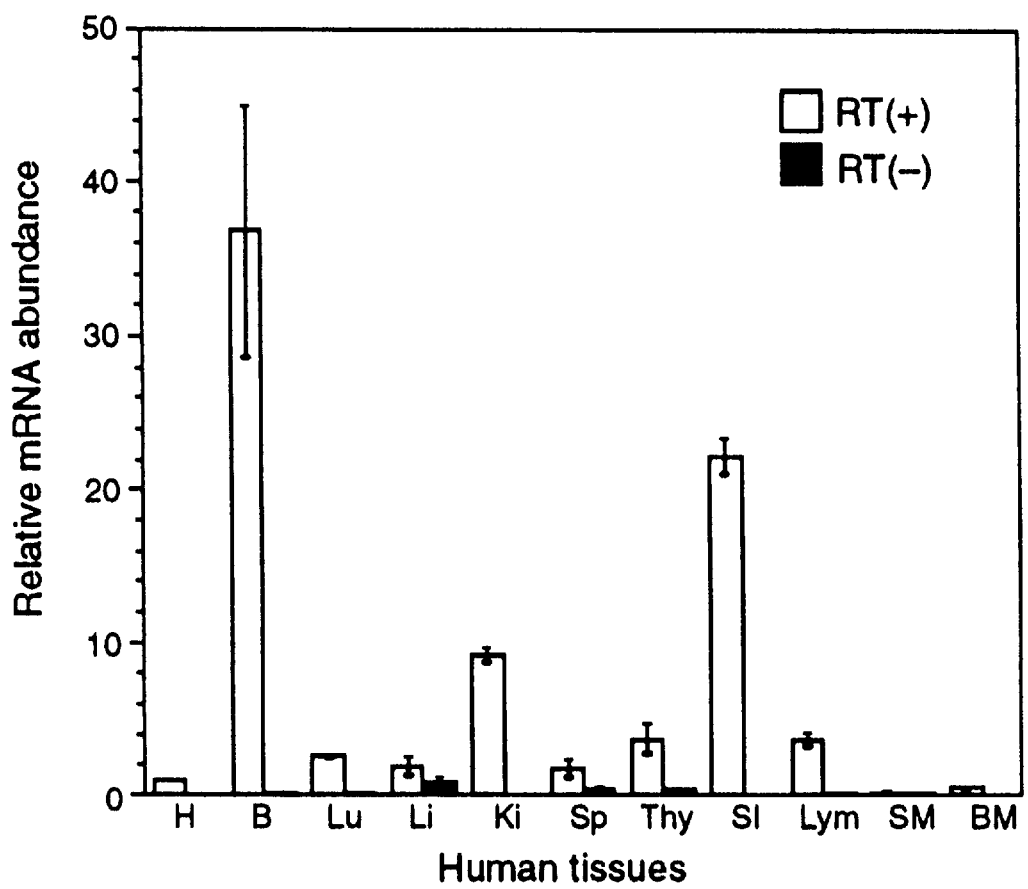
FIG. 7B shows the results of real time quantitative RT-PCR analysis of expression of IFN-ε in different tissues. PolyA+RNA from human tissues was subjected to TaqMAN RT-PCR analysis (details of which are described in Example 10). Signals were normalized to the house keeping gene RPL19 and the expression level was plotted as fold change relative to the signal from heart tissue. H=heart; B=brain; Lu=lung; Li=liver, Ki=kidney, Sp=spleen; Thy=thymus; SI=small intestine; Lym=lymph node; SM=smooth muscle; BM=bone marrow. Parallel reactions with or without reverse transcriptase were plotted as striped or solid bars respectively in order to estimate the signal from potential contaminating genomic DNA. Error bars represent standard derivation from three experiments.

Measurements of 10 specifically labeled chromosomes 9 demonstrated that F480 is located at a position which is 51% of the distance from the centromere to the telomere of the 9p, an area which corresponds to chromosome 9p21.2-21.3 (FIG. 7(B)). A total of 80 metaphase cells were analyzed with 72 exhibiting specific labeling. The identified location is near other type I interferons (DeMaeyer, E. and De. Maeyer-Guignard, J., *Interferons. The Cytokine Handbook*, 2nd ed., 265–288 [1994]). Sequencing of the F480 BAC clone indicates that like other type I interferons, the IFN-ε gene has no intervening sequences in its coding region.

Example 9

Northern Blot Analysis

The expression of IFN-ε in multiple tissues was examined by quantitative RT-PCR (TaqMan® Technology).

A multi-tissue RNA blot containing 2 μg each of poly (A)+RNA from human tissues was purchased from Clontech. An overlapping oligo corresponding to codons for amino acid 2–31 in the IFN-ε precursor was generated. The DNA probes were labeled with $\alpha$-$^{32}$P=dCTP by random priming (Promega). The RNA blot was hybridized with 50% formamide, 5×SS, 50 mM potassium phosphate (pH 7.0), 5×Denhardt's solution, 10% dextran sulfate at 42° C. for 20 hours. The blot was washed with 0.1×SSC, 0.1% SDS at 50° C. for 30 minutes and exposed in Phospholmager.

The following tissues were exarnined: adult 1) heart, 2) brain, 3) placenta, 4) lung, 5) liver, 6) skeletal muscle, 7) kidney, 8) pancreas, 9) spleen, 10) thymus, 11) prostate, 12) testis, 13) ovary, 14) small intestine, 15) colon (mucosal lining), and 16) peripheral blood leukocytes, and human fetal tissues: 17) brain, 18) lung, 19) liver, and 20) kidney. Low levels of constitutive expression were detected in tissues of brain, lung, kidney, and small intestine (data not shown).

Example 10

Characterization and Biological Activities of IFN-ε

Protocols

Expression and Purification of Recombinant IFN-ε in *E. coli*

IFN-ε was expressed in the *E. coli* cytoplasm, using a derivative of the tryptophan (trp) promoter vector pHGH207-1 (DeBoer et al., *Promoter Structure and Function*, Rodriguez et al., eds., p. 462, Praeger, New York, 1982.) A 210 amino acid leader sequence was fused to the amino termini of the mature interferon to ensure efficient translation initiation and to facilitate purification. This leader encodes the first 6 amino acids of the STII signal sequence (Picken et al., *H. Infect. Immun.* 42, 269–275 [1983]), followed by 8 histidines, and finally the amino acid sequence ASDDDDK for potential cleavage by the protease enterokinase. Downstream of the leader and mature IFN-ε coding sequences was placed the λ to transcriptional terminator (Scholtissek and Grosse, *Nucl. Acids Res.* 15, 3185 [1987]).

The expression plasmid was transformed into the *E. coli* host 52A7 (W3110 fhuA(tonA) lon galE rpoHts(htpRts) clpP lacIq) prior to the induction of the trp promoter. Cells were first grown in LB containing ampicillin at 30° C. until a cell density of 2–4 ($A_{600}$) was reached. The LB culture was then diluted 20 fold into a high cell density tryptophan limiting media (per liter: 1.86 g $Na_2HPO_4$, 0.93 g $NaH_2PO_4H_2O$, 3.57 g $(NH_4)_2SO_4$, 0.71 g $Na_2Citrate(H_2O)_2$, 1.07 g KCl, 5.36 g yeast extract, 5.36 g casamino acids, autoclave, then add MOPS pH7.3 to 110 mM, $NgSO_4$ to 7 mM, and glucose to 0.55% w/v). After 5 hours, trans-3-indoleacrylic acid was added to 50 μg/mL and then growth was continued for another 16 hours at 30° C. with shaking.

*E. coli* paste from 0.5 liter fermentations was resuspended in 10 volumes (w/v) in 7 M guanidine, 20 mM Tris, pH 8 buffer. Solid sodium sulfite and sodium tetrathionate were added to final concentrations of 0.1 M and 0.02 M, and stirred overnight at 40° C. After centrifugation, the supernatant was diluted in metal chelate column buffer (6 M guanidine, 20 mM Tris, pH 7.4) and subjected to Ni-NTA metal chelate column (Quiagen). Eluted IFN-ε was refolded by diluting the metal chelate purified protein slowly into freshly prepared refolding buffer consisting of: 20 mM Tris, pH 8.6, 0.3 M NaCl, 5 mM cysteine, 20 mM glycine, 40 μg/m; polyethylene glycol (3350 MW) and 1 mM EDTA. The refolded protein was chromatographed on a Poros R1/H reversed phase column (PerSeptive). Quantitative amino acid analysis was used to determine protein concentrations.

Expression and Purification of IFN-α receptor (IFNAR) Immunoadhesins

Mammalian expression vectors encoding IFN-αR1-IgG1 and IFN-αR2-IgG1 (pRKIFN-α/β-IgG and pRKIFN-α/β-IgG) were constructed from plasmids encoding the human type 1 interferon receptors (pRKIFN-α/βR1 and pRKIFN-α/β-R2) and CD4-IgG1 (pRKCD4$_2$Fc$_1$- Capon et al., *Nature* 337:525–531 [1989]). The mature IFN-α/βR1-IgG and IFN-α/βR2-IgG polypeptide encoded by pRKIFN-α/βR1-IgG and pRKIFN-α/βR2-IgG thus contain 633 and 443 amino acids, respectively. The IFN-α/βR-IgGs were expressed in human embryonic kidney 293 cells by transient transfection with the respective plasmids, using the calcium phosphate precipitation method. The receptor-IgG immunoadhesins were purified to greater than 95% homogeneity from serum-free cell supernatants by affinity chromatography on Staphylococcus aureus Protein A. The immunoadhesins were eluted with 50 mM sodium citrate pH 3 / 20% (w/v) glycerol, and the pH was neutralized with 0.05 volumes of 3M TRIS HCl (pH 8–9).

Tyrosine Phosphorylation Assay

Cells were serum-starved for 6 hours and subjected to treatment of cytokines for the indicated period of time, using the indicated concentrations. The lysis of cells, immunoprecipitation, Western blot and ECL detection were performed as previously described by Zhang et al., *Proc. Natl. Acad. Sci. USA* 94, 9562–7 (1997). The following antibodies were used: JAK1 (Q-19), JAK2 (HR758) Tyk2 (C-20), Stat1 (C-111), Stat2 (C-20) and Stat3 (C-20) purchased from Santa Cruz Biotechnology (CA). Antibody 4G10 was purchased from Upstate Biotechnology. anti-IFN-αR1 antibody 2E1.5.2 and anti-IFN-αR2 antibody 3B7.22.7 were prepared as described in Lu J. et al., *J. Immunol.* 160: 1782–1788 (1998).

Electrophoretic Mobility Shift Assay (EMSA)

HelaS3 (ATCCCCL2.2) cells were pretreated with IFN-γ (100 U/ml) overnight to increase the expression of p48 (Levy et al., *Genes Dev.* 3, 1362–71 [1989]). Cells were treated with IFN-ε$^{His}$ or IFN-α for 45 minutes and nuclear extract was prepared. The preparation of nuclear extract and EMSA followed the protocol described by Levy, supra, with modifications (Zhang et al., *J. Biol. Chem.* 271, 95–3–9 [1996]). The probe for ESRE (ISG-15) and SIE is based on Darnell et al., *Science* 264, 1415–21 (1994).

Cell Culture, FACS analysis and Antiproliferation and Antiviral Assays

A549 cells (ATCC CCL-185.1, human lung carcinoma) and human 293 cell lines (ATCC 45504, kidney epithelial) were growth in "50:50" medium (HAM's F12: Dulbecco's Modified Eagle medium), with 10% FBS. Daudi cells. MELT-4 and U266 were growth in RPMI1640, supplemented with 10% FBS. Daudi cells (ATCC CCL-213, B lymphoblast), MLT-4 (ATCC CRL-1582, T lymphoblast) and U266 (ATCC TIB-196, lymphoblast) cells were grown in RPMI 1640 with 10% FBS.

FACS analysis was performed as previously described (Zhang, 1997, supra). The anti-MHC I antibody (HLA-A, B, C) was purchased from Pharmacia.

The antiproliferation assay was performed as described by Evinger and Pestka, *Methods Enzamol.* 79, 362–8 (1981) with the following modifications. Daudi cells were treated with different doses of IFNs in the presence or absence of antagonistic antibodies in 96-well culture plates at $5 \times 10^5$ cells/ml, and incubated at 37° C. for 72 hours. One tenth volume of AlamarBlue reagent was added to the culture and the cells were incubated for 4 hours before measuring the fluorescent intensity as a indicator of cell proliferation (Alamar Biotechnology, Sacramento, Calif.).

Antiviral analysis was performed as described Rubinstein et al., *J. Virol.* 37, 755–758 (1981). Briefly, cells were seeded into 96-well culture plates and allowed to grow for 24 hours before IFN-ε treatment. EMCV challenge at 1 multiplicity of infection unit/well was performed 24 hours after the IFN-ε treatment and the cells were allowed to be infected for another 24 hours. Cell survival was quantified by crystal violet dye exclusion.

Results

A search of an expressed sequence tag (EST) database for sequences related to Type I IFN family members revealed an EST that was predicted to encode a polypeptide bearing about 38% amino acid sequence identity to amino acids 58–148 of IFN-α14. Using probes based on the EST, a cDNA was cloned and found to encode an ORF of 208 amino acids (FIG. 1) with a potential signal sequence of 21 amino acids and a calculated molecular weight of 21.9 kD. Analysis of the amino acid sequence revealed that it contained homology to Type I IFN family members (e.g. about 33% and 37% sequence identity to IFN-α2 and IFN-β, respectively). Progressive alignment analysis (Feng, D. F. and Doolittle, R. F., *Meth. Enzymol.* 183, 375–387 [1990]) of the encoded protein and other Type I IFNs indicates that the protein sequence defines a new branch of the Type I IFN family (FIG. 5). We therefore named this gene product IFN-ε.

IFN-ε contains two potential sites for N-linked glycosylation at positions 74 and 83 (predicted mature protein, thereafter). A pair of Cys residues (Cys32 and Cys 142) that are conserved in all human type I IFNs and are known to form a disulfide linkage crucial for activity (Morehead et al., *Biochemistry* 23, 2500–2507 [1984]) are also conserved in IFN-ε. A second pair of cysteines that are present in IFN-α and -ω (e.g. Cys1 and Cys98 g in IFN-α) and form a disulfide bridge are not conserved in IFN-ε. Instead, IFN-ε has a cysteine at position 154 that is not conserved in other Type I IFNs. Despite the limited sequence identity to other IFNs, molecular modeling suggests that IFN-ε displays similar tertiary structure compared to IFN-α (L. Presta, data not shown).

As described earlier. a BAC clone (F480) encodino the IFN-ε gene was isolated. This clone was used to map the chromosomal location by fluorescent in situ hybridization (FISH). These studies localized the IFN-ε gene to chromosome 9p21.2-21.3 (FIG. 7A), placing it near the human IFN-ω, IFN-β and a cluster of IFN-α genes that have been mapped to 9p22-p13 (De Maeyer, E. and DeMaeyer-Guignard, J., supra).

The expression of IFN-ε in different human tissues was examined by real time quantitative RT-PCR (TaqMan® technology) using tissue-specific polyA+RNA from adult humans as templates (FIG. 7B). The highest expression of IFN-ε mRNA was observed in the brain, kidney, and small intestine. Several other tissues have lower levels of expression, including the lung, liver, spleen, thymus and lymph node, whereas heart and bone marrow shoed low levels of mRNA expression. Thus, IFN-ε mRNA is expressed constitutively in various adult tissues. We have not detected significant poly(I).poly© induction of IFN-ε mRNA in human fibroblasts or in Daudi cells. In contrast, human Mx gene expression was greatly induced in these cells and IFN-β transcription was upregulated in fibroblasts (data not shown).

IFN-ε protein was expressed in *E. coli* with an amino terminal His targ and purified by Ni-NTA affinity chromatography. To determine whether IFN-ε can activate known Type I IFN receptors, we treated lymphoblast U266 cells with the recombinant IFN-ε (designated IFN-ε$^{His}$) of various concentrations and observed a dose dependent increase in tyrosine phosphorylation of both receptor subunits. IFN-αR1 and IFN-αR2 (the long form, or IFN-αR2c) (FIGS. 8A–B). This induction of receptor tyrosine phosphorylation was a rapid response, starting at less than 1 minute after treatment, peaking at 15 minutes and decreasing to undetectable levels by one hour (data not shown). Similar results were obtained with other cell lines such as the T lymphoblast cell line MOLT-4 and the B lymphoblast cell line Daudi (not shown).

IFNs and other cytokines have been shown to activate JAK-STAT signaling components after interacting with their receptors. To determine if IFN-ε activates the JAK-STAT pathway, we assayed tyrosine phosphorylation of the key components in the IFN signal pathway. As shown in FIGS. 8C–D, IFN-ε stimulated tyrosine phosphorylation of Janus kinase members JAK1 and Tyk2, but not JAK2 (not shown). It also induced tyrosine phosphorylation of Stat1, Stat2 and Stat3. In addition, we examined the formation of transcription factor complexes interferon-stimulated gene factor 3 (ISGF3) and serum-induced factor (SIF) (Darnell et al., *Science* 964, 1415–1421 [1994]) upon treatment of HeLa cells with IFN-ε (FIG. 8E). Like IFN-α, IFN-ε stimulated the formation of ISGF3 and SIF. These complexes can be specifically competed by excess amounts of cold oligonucleotides and can be abolished or supershifted by anti-Stat antibodies. Therefore, like other type I IFNs, IFN-ε activates STAT-1, -2, and -3 and leads to the formation of transcription complexes ISGF3 and SIF.

We used antagonistic antibodies directed against IFN-αR1 and IFN-αR2 to determine if the known IFN-α receptor subunits are required for IFN-ε induced activation of JAK-STAT signaling. These monoclonal antibodies have previously been shown to inhibit the antiviral response of IFN-α (Lu et al., (1998) supra). These antibodies recognize the corresponding receptor specifically and inhibit IFN-α2a-induced State2 tyrosine phosphorylation in MOLT-4 cells (FIG. 8F). These same antibodies also inhibited IFN-ε -induced tyrosine phosphorylation of Stat2. In fact, the anti-IFN-α-R1 antibody was a more potent inhibitor of IFN-ε activity than of IFN-α2a activity (FIG. 8F). We conclude from these experiments that IFN-αR1 and IFN-αR2 are necessary for IFN-ε to stimulate the JAK-STAT pathway. However, we have not ruled out the possibility that other receptor component(s) are involved in the IFN-ε -receptor interaction.

Figure 10:
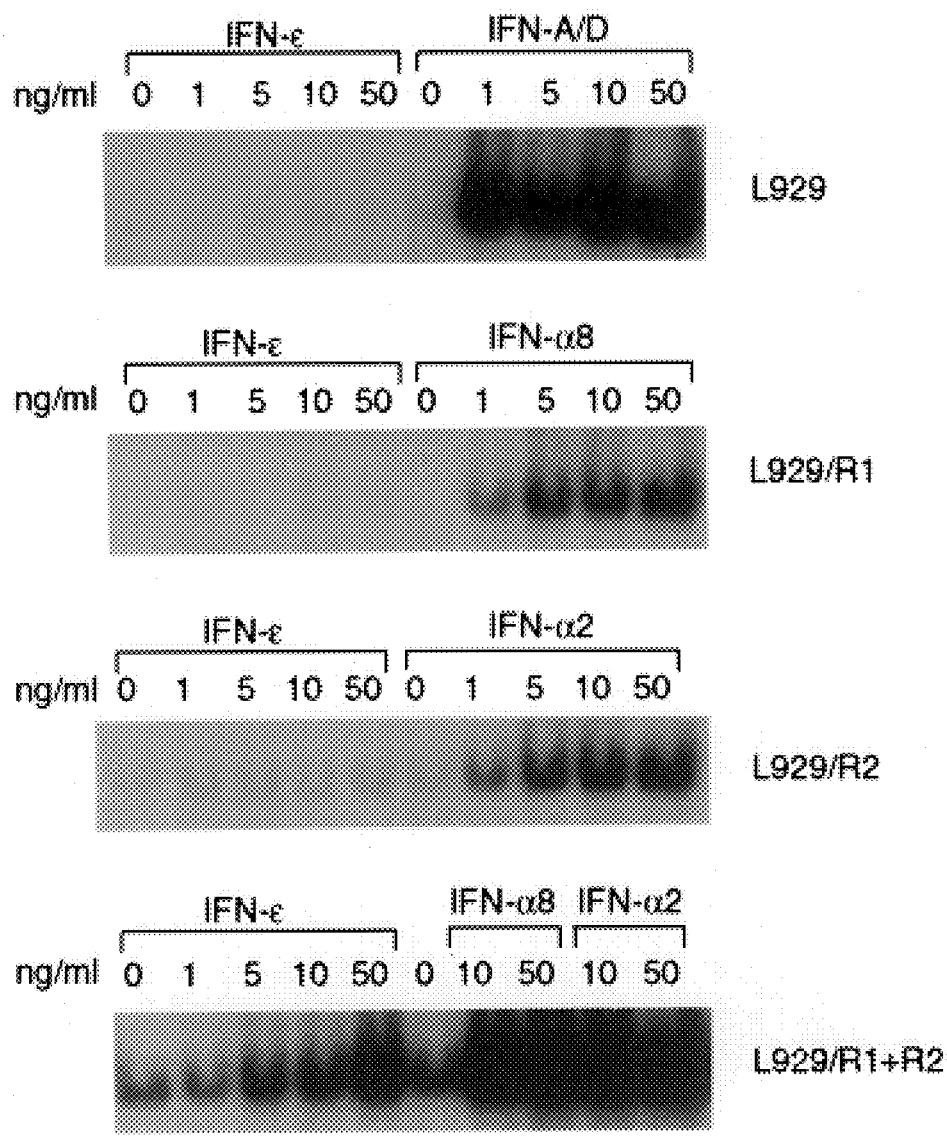
FIG. 10 Cell lines that express IFN-αR1, IFN-αR2c or both receptors were designated L929/R1, L929/R2, L929/R1+R2, respectively (indicated at the right of each panel). $10^7$ cells of each line were treated with IFNs using the indicated concentrations. Formation of ISGF3 was examined by EMSA as described in Example 10.

The subtype of human IFN to which murine cells respond is dependent upon whether the IFN is species specific and whether the cells express human IFN-αR2 or IFN-αR2. Expression of human IFN-αR1 in L929 cells renders them responsive to human IFN-α3, but not human IFN-α2 (Gibbs et al., *J. Biol. Chem.* 271, 28710–28716 [1996]). Conversely L929 cells that express human IFN-αR2 respond to human IFN-α2 but not human IFN-α3. We took advantage of the species specificity of the IFN receptor by analyzing human IFN-α and IFN-ε induced ISGF3 complex formation in mouse L929 cells stably transfected with human IFN-αR1 or IFN-αR2 or both. Expression of either IFN-αR alone was not sufficient to confer sensitivity to IFN-ε (FIG. 10). Strikingly, IFN-ε induced dramatic elevation in ISGF3 formation in L929 cells expressing both IFN-αR1 and IFN-αR2. This result indicates that IFN-ε is a human species-specific interferon, it requires both human IFN-αR subunits to signal in murine cells. It also suggests that potential differences exist between the interaction of the IFN-αR with IFN-ε and the interaction of the IFN-αR with other type I IFNs.

Figure 9A:
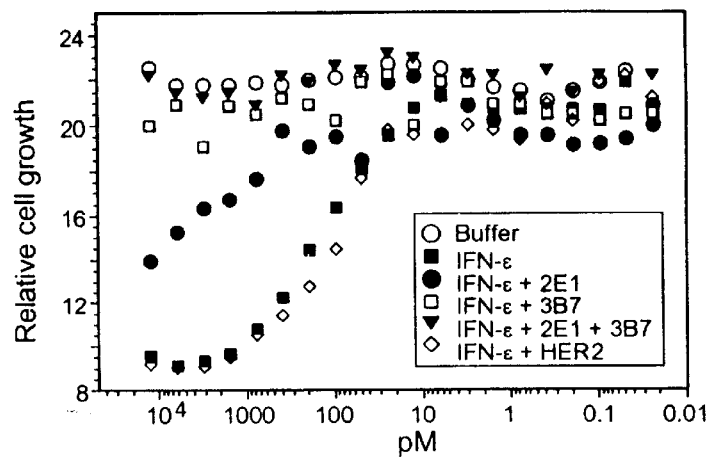
FIGS. 9A–C Biological activities of IFN-ε: antiproliferation, induction of MHCI expression and antiviral effects. (A) IFN-ε has growth inhibitory effect on Daudi cells. Daudi cells ($4\times10^5$/ml) were treated with IFN-ε of various concentrations in the presence or absence of 0.5 μg/ml of monoclonal antibodies anti-IFN-αR1 (2E1), anti-IFN-αR2 (3B7) or control antibody anti-HER2 for 72 hours. Cell proliferation was examined by AlamarBlue assay. At least three experiments were performed and a representative result is shown. (B) IFN-ε stimulates MHC I expression in MOLT-4 cells. MOLT-4 cells ($4\times10^5$/ml) were treated with indicated concentrations of IFN-ε$^{His}$ for 72 hours. FACS analysis was performed using antibodies against NHC I (HLA-A, B, C, Pharminogen). (ε) IFN-ε protects WISH cells from EMCV induced cytopathic effect. Cells were pretreated with IFN-ε for 24 hours and challenged with EMVC for an additional 24 hours. Cell survival was estimated by crystal violet dye exclusion assay and plotted as percentage of non-virus control. Error bars represent standard deviation (n=3).
Figure 9B:
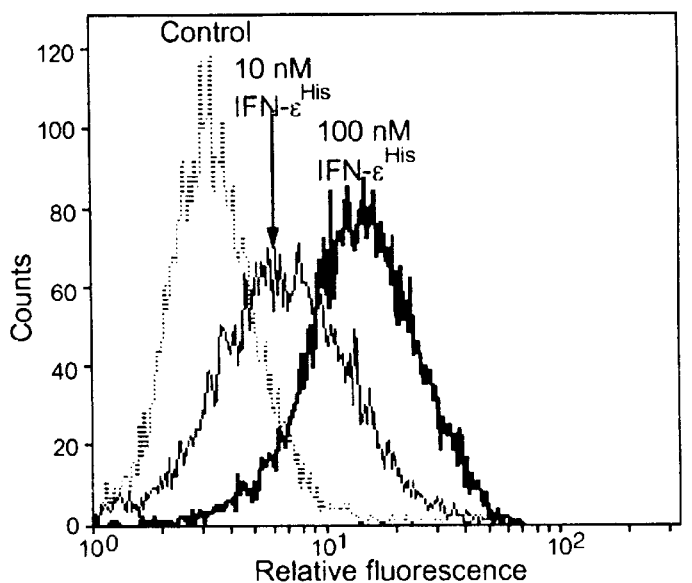
Figure 9C:
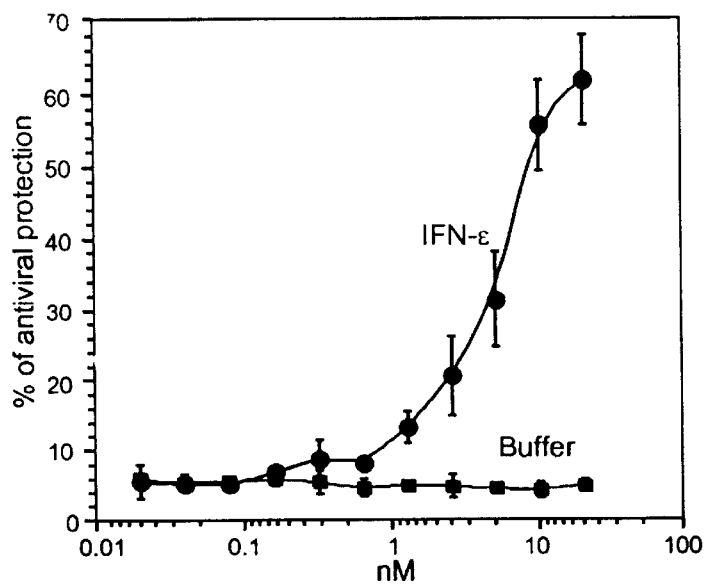

To explore the biological activities of IFN-ε, we first evaluated its antiproliferative effect. Daudi cells were treated with increasing concentrations of IFN-ε$^{His}$, and cell proliferation was measured by Alamar-Blue assay (FIG. 9A) and confirmed by cell counting (data not shown). Antibodies that block the functions of IFN-αR1 (2E1) and IFN-αR2 (3B7) were included in the assay. IFN-ε inhibited proliferation of Daudi cells in a dose dependent fashion. The antibodies completely (for 3B7) or partially (for 2E1) blocked the growth inhibition effect of IFN-ε at a concentration of 0.5 μg/ml. The blocking effect of 2E1 was 100% at concentrations higher than 5 μg/ml (data not shown). In contrast, a control antibody against the receptor tyrosine kinase HER2 did not block IFN-ε activity. Second, we used several cell lines to evaluate MHCI expression as an indication of immune modulation. IFN-ε increased the expression of MHC I in MOLT-4 (FIG. 9B), U266 and Daudi cells (data not shown) in dose dependent manner. MHC II expression was not induced by IFN-ε in these cells (data not shown). Finally, to test if IFN-ε exhibits antiviral activity, human amniotic WISH cells were challenged with encephalomyocarditis virus (EMCV) and the protective effect of IFN-ε was examined in a cytopathic assay. Pretreatment of these cells by IFN-ε protected WISH cells from an EMCV-induced cytopathic effect (FIG. 9C). A similar result was obtained using A549 cells challenged with EMCV (data not shown).

Discussion

In summary, from analysis of sequence homology, chromosomal localization, receptor interaction, downstream signaling and biological effects, it can be concluded that IFN-ε belongs to a novel family of Type I IFNs. Phylogenetic analysis of the human IFNs indicates that IFN-ε is nearly equally divergent from the IFN-α cluster, IFN-ω, and IFN-β (FIG. 5). Therefore, IFN-ε defines a novel type I IFN, and is likely to have evolved from a common ancestor by successive gene duplication. Like other type I IFNs, the IFN-ε is intronless (data not shown).

Although IFN-ε shares common features with other type I IFNs, it is unique in several aspects.

First, IFN-ε is constitutively expressed in multiple adult tissues with a pattern that differs from that of IFN-α or IFN-β (FIG. 7A–B). The fact that IFN-ε transcription was detected in the brain suggests that it may play a role in neuronal modulation. Neuronal activity and growth were found to be modulated by other type I interferons (Dafny et al., *Brain Res.* 734, 269–274 [1996]; Pliopsys and Massimini, *Neuroimmunomodulation* 2, 31–5 [1995]). In contrast to the IFN-β gene, the IFN-ε gene appears only marginally inducible by poly(I).poly© in human fibroblasts which suggests it may be regulated by different inducers.

Second, the low degree of sequence homology between other type I interferon proteins and IFN-ε has indicated that the receptor interaction between IFN-ε and IFN-αR might differ from the interaction of the same receptor with other type I interferons. Indeed, we have experimentally found differences in the interaction between the IFN-αR and IFN-ε and for other type I interferons. IFN-αR2 has been shown to bind type I interferons in vitro. While we observed binding of other type I IFNs to IFN-αR2 in vitro, we did not detect significant binding of IFN-ε to either IFN-αR1 or IFN-αR2 alone. In contrast to results with human IFN-α2 and IFN-α3, we reconstituted IFN-ε signaling in L929 cells only when human IFN-α1 and human IFN-α2 were coexpressed (FIG. 10). In contrast, expression of either IFN-αR1 or IFN-αR2 alone was not sufficient to confer sensitivity to IFN-ε. This result indicates that IFN-ε requires both human IFN-αR subunits to signal in murine cells and suggests potential differences in the interactions of the IFN-αR with IFN-ε and other type I IFNs.

To explore the biological activities of IFN-ε, we first evaluated the growth inhibitory effect of this interferon. Daudi cells were treated with increasing concentrations of IFN-ε$^{His}$ and cell proliferation was measured by an Alamar Blue assay (FIG. 4A), and confirmed by cell counting (data not shown). Antibodies that block the functions of IFN-αR1 (2E1) and IFN-αR2 (3B7) were included in the assay. IFN-ε inhibited proliferation of Daudi cells in a dose dependent fashion. Consistent with the result from Stat2 activation (FIG. 3F), the antibodies completely (for 3B7) or partially (for 2E1) blocked the growth inhibition effect of IFN-ε at a concentration of 0.5 μg/ml. The blocking effect of 2E1 was 100% at concentrations higher than 5 μg/ml (data not shown). In contrast, a control antibody against the receptor tyrosine kinase HER2 did not block IFN-ε activity. Second, we used several cell lines the evaluate MHC I expression as a indication of immune modulation. IFNε induced the expression of MHC I in MOLT-4 (FIG. 9B), U266 and Daudi cells (data not shown) in a dose dependent manner. MHC II expression was not induced by IFN-ε in these cells (data not shown). Finally, to test if IFN-ε exhibits antiviral activity, human amniotic WISH cells were challenged with encephalomycarditis virus (EMCV) and the protective effect of IFN-ε was examined in a cytopathic assay. Pretreatment of these cells by IFN-ε protected WISH cells from EMCV induced cytopathic effect (FIG. 9C). A similar result was obtained using 549 cells challenged with EMCV (data not shown).

The specific activities of IFN-ε$^{His}$ to stimulate these biological results are lower than purified IFN-αR1a (1–2 logs lower in JAK-STAT signaling and 2–3 logs lower in biological assays). This could indicate either a physiologically relevant and inherently lower specific activity of IFN-ε in these particular assays, or may reflect the manner in which the epitope-tagged recombinant protein was prepared. It is possible that in vivo, IFN-ε is expressed at higher levels in some tissues and thus the lower potency observed in vitro reflects the physiological situation. Alternatively, the nature of ligand-receptor interaction is different between IFN-ε and other Type I IFNs. In addition, IFN-ε$^{His}$ is a His-tagged recombinant protein, factors such as protein folding may affect specific activity. Further experiments are needed to elucidate the unique character of IFN-ε, which include detailed ligand-receptor interact ion studies and comparison of various activities between members of the Type I interferon family.

Deposit of Material

The following material has been deposited with the American Type Culture Collection, 12301 Parklawn Drive, Rockville, Md., USA (ATCC):

| Material | ATCC Dep. No. | Deposit Date |
| --- | --- | --- |
| DNA50960-1224 | 209509 | December 3, 1997 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

SEQUENCE LISTING

<160> NUMBER OF SEQ ID NOS: 12

<210> SEQ ID NO 1
<211> LENGTH: 208
<212> TYPE: PRT
<213> ORGANISM: Homo sapiens

<400> SEQUENCE: 1

```
Met Ile Ile Lys His Phe Phe Gly Thr Val Leu Val Leu Leu Ala
 1               5                  10                  15

Ser Thr Thr Ile Phe Ser Leu Asp Leu Lys Leu Ile Ile Phe Gln
                20                  25                  30

Gln Arg Gln Val Asn Gln Glu Ser Leu Lys Leu Leu Asn Lys Leu
                35                  40                  45

Gln Thr Leu Ser Ile Gln Gln Cys Leu Pro His Arg Lys Asn Phe
                50                  55                  60

Leu Leu Pro Gln Lys Ser Leu Ser Pro Gln Gln Tyr Gln Lys Gly
                65                  70                  75

His Thr Leu Ala Ile Leu His Glu Met Leu Gln Gln Ile Phe Ser
                80                  85                  90

Leu Phe Arg Ala Asn Ile Ser Leu Asp Gly Trp Glu Glu Asn His
                95                  100                 105

Thr Glu Lys Phe Leu Ile Gln Leu His Gln Gln Leu Glu Tyr Leu
                110                 115                 120

Glu Ala Leu Met Gly Leu Glu Ala Glu Lys Leu Ser Gly Thr Leu
                125                 130                 135

Gly Ser Asp Asn Leu Arg Leu Gln Val Lys Met Tyr Phe Arg Arg
                140                 145                 150

Ile His Asp Tyr Leu Glu Asn Gln Asp Tyr Ser Thr Cys Ala Trp
                155                 160                 165

Ala Ile Val Gln Val Glu Ile Ser Arg Cys Leu Phe Phe Val Phe
                170                 175                 180

Ser Leu Thr Glu Lys Leu Ser Lys Gln Gly Arg Pro Leu Asn Asp
                185                 190                 195

Met Lys Gln Glu Leu Thr Thr Glu Phe Arg Ser Pro Arg
                200                 205
```

<210> SEQ ID NO 2
<211> LENGTH: 1502
<212> TYPE: DNA
<213> ORGANISM: Homo sapiens

<400> SEQUENCE: 2

```
cttagatatt aaactgatag gataagatat aaataatttt aagattgctg           50
atatatgttt taaaattaat tatttgctca agcatttgtg acaatttaca          100
gttctaattg aggttttaaa tttagtagtt tgtaggtatt ttaagttttg          150
cccctgaatt ctttataggt gctgataagc ctttggttaa gttttactcc          200
```

-continued

```
atgaaagact attactgaaa aaaatgtaat ctcaataaaa gaactttaat      250
aagcttgact aaatatttag aaagcacatt gtgttcagtg aaactttgta      300
tataatgaat agaataataa aagattatgt tggatgacta gtctgtaatt      350
gcctcaagga aagcatacaa tgaataagtt attttggtac ttcctcaaaa      400
tagccaacac aatagggaaa tggagaaaat gtactctgaa caccatgaaa      450
agggaacctg aaaatctaat gtgtaaactt ggagaaatga cattagaaaa      500
cgaaagcaac aaaagagaac actctccaaa ataatctgag atgcatgaaa      550
ggcaaacatt cactagagct ggaatttccc taagtctatg cagggataag      600
tagcatattt gaccttcacc atgattatca agcacttctt tggaactgtg      650
ttggtgctgc tggcctctac cactatcttc tctctagatt tgaaactgat      700
tatcttccag caaagacaag tgaatcaaga agtttaaaa ctcttgaata       750 agttgcaaac cttgtcaatt cagcagtgtc taccacacag gaaaaacttt      800
ctgcttcctc agaagtcttt gagtcctcag cagtaccaaa aaggacacac      850
tctggccatt ctccatgaga tgcttcagca gatcttcagc ctcttcaggg      900
caaatatttc tctggatggt tgggaggaaa accacacgga gaaattcctc      950
attcaacttc atcaacagct agaataccta gaagcactca tgggactgga      1000
agcagagaag ctaagtggta ctttgggtag tgataacctt agattacaag      1050
ttaaaatgta cttccgaagg atccatgatt acctggaaaa ccaggactac      1100
agcacctgtg cctgggccat tgtccaagta gaaatcagcc gatgtctgtt      1150
ctttgtgttc agtctcacag aaaaactgag caaacaagga agacccttga      1200
acgacatgaa gcaagagctt actacagagt ttagaagccc gaggtaggtg      1250
gagggactag aggacttctc cagacatgat tcttcataga gtggtaatac      1300
aatttatagt acaatcacat tgctttgatt ttgtgtatat atatatttat      1350
ctgagtttta agattgtgca tattgaccac aattgttttt attttgtaat      1400
gtggctttat atattctatc cattttaaat tgtttgtatg tcaaaataaa      1450
ttcattaata tggttgattc ttcaaaaaaa aaaaaaaaaa aaaaaaaaa       1500 aa                                                         1502
```

<210> SEQ ID NO 3
<211> LENGTH: 276
<212> TYPE: DNA
<213> ORGANISM: Homo sapiens
<220> FEATURE:
<221> NAME/KEY: unsure
<222> LOCATION: 114
<223> OTHER INFORMATION: unknown base

<400> SEQUENCE: 3

```
cttcggaagt acattttaac ttgtaatcta aggttatcac tacccaaagt       50
accacttagc ttctctgctt ccagtcccat gagtgcttct aggtattcta      100
gctgttgatg aagntgaatg aggaatttct ccgtgtggtt ttcctcccaa      150
ccatccagag aaatatttgc cctgaagagg ctgaagatct gctgaagcat      200
ctcatggaga atgccagag tgtgtccttt ttggtactgc tgaggactca       250
aagacttctg aggaagcaga aagttt                              276
```

<210> SEQ ID NO 4
<211> LENGTH: 25
<212> TYPE: DNA
<213> ORGANISM: Homo sapiens

<400> SEQUENCE: 4
tctctgcttc cagtcccatg agtgc                                                                      25

<210> SEQ ID NO 5
<211> LENGTH: 27
<212> TYPE: DNA
<213> ORGANISM: Homo sapiens

<400> SEQUENCE: 5
gcttccagtc ccatgagtgc ttctagg                                                                    27

<210> SEQ ID NO 6
<211> LENGTH: 50
<212> TYPE: DNA
<213> ORGANISM: Homo sapiens

<400> SEQUENCE: 6
ggccattctc catgagatgc ttcagcagat cttcagcctc ttcagggcaa                                            50

<210> SEQ ID NO 7
<211> LENGTH: 188
<212> TYPE: PRT
<213> ORGANISM: Homo sapiens

<400> SEQUENCE: 7

```
Met Ala Leu Thr Phe Ala Leu Leu Val Ala Leu Leu Val Leu Ser
 1               5                  10                  15

Cys Lys Ser Ser Cys Ser Val Gly Cys Asp Leu Pro Gln Thr His
                20                  25                  30

Ser Leu Gly Ser Arg Arg Thr Leu Met Leu Leu Ala Gln Met Arg
                35                  40                  45

Lys Ile Ser Leu Phe Ser Cys Leu Lys Asp Arg His Asp Phe Gly
                50                  55                  60

Phe Pro Gln Glu Glu Phe Gly Asn Gln Phe Gln Lys Ala Glu Thr
                65                  70                  75

Ile Pro Val Leu His Glu Met Ile Gln Gln Ile Phe Asn Leu Phe
                80                  85                  90

Ser Thr Lys Asp Ser Ser Ala Ala Trp Asp Glu Thr Leu Leu Asp
                95                 100                 105

Lys Phe Tyr Thr Glu Leu Tyr Gln Gln Leu Asn Asp Leu Glu Ala
               110                 115                 120

Cys Val Ile Gln Gly Val Gly Val Thr Glu Thr Pro Leu Met Lys
               125                 130                 135

Glu Asp Ser Ile Leu Ala Val Arg Lys Tyr Phe Gln Arg Ile Thr
               140                 145                 150

Leu Tyr Leu Lys Glu Lys Lys Tyr Ser Pro Cys Ala Trp Glu Val
               155                 160                 165

Val Arg Ala Glu Ile Met Arg Ser Phe Ser Leu Ser Thr Asn Leu
               170                 175                 180

Gln Glu Ser Leu Arg Ser Lys Glu
               185
```

```
<210> SEQ ID NO 8
<211> LENGTH: 195
<212> TYPE: PRT
<213> ORGANISM: Homo sapiens

<400> SEQUENCE: 8

Met Ala Leu Leu Phe Pro Leu Ala Ala Leu Val Met Thr Ser
 1               5                  10                  15

Tyr Ser Pro Val Gly Ser Leu Gly Cys Asp Leu Pro Gln Asn His
                20                  25                  30

Gly Leu Leu Ser Arg Asn Thr Leu Val Leu Leu His Gln Met Arg
            35                  40                  45

Arg Ile Ser Pro Phe Leu Cys Leu Lys Asp Arg Arg Asp Phe Arg
        50                  55                  60

Phe Pro Gln Glu Met Val Lys Gly Ser Gln Leu Gln Lys Ala His
    65                  70                  75

Val Met Ser Val Leu His Glu Met Leu Gln Gln Ile Phe Ser Leu
80                  85                  90

Phe His Thr Glu Arg Ser Ser Ala Ala Trp Asn Met Thr Leu Leu
            95                  100                 105

Asp Gln Leu His Thr Gly Leu His Gln Gln Leu Gln His Leu Glu
        110                 115                 120

Thr Cys Leu Leu Gln Val Val Gly Glu Gly Glu Ser Ala Gly Ala
    125                 130                 135

Ile Ser Ser Pro Ala Leu Thr Leu Arg Arg Tyr Phe Gln Gly Ile
            140                 145                 150

Arg Val Tyr Leu Lys Glu Lys Lys Tyr Ser Asp Cys Ala Trp Glu
        155                 160                 165

Val Val Arg Met Glu Ile Met Lys Ser Leu Phe Leu Ser Thr Asn
    170                 175                 180

Met Gln Glu Arg Leu Arg Ser Lys Asp Arg Asp Leu Gly Ser Ser
            185                 190                 195

<210> SEQ ID NO 9
<211> LENGTH: 187
<212> TYPE: PRT
<213> ORGANISM: Homo sapiens

<400> SEQUENCE: 9

Met Thr Asn Lys Cys Leu Leu Gln Ile Ala Leu Leu Leu Cys Phe
 1               5                  10                  15

Ser Thr Thr Ala Leu Ser Met Ser Tyr Asn Leu Leu Gly Phe Leu
                20                  25                  30

Gln Arg Ser Ser Asn Phe Gln Cys Gln Lys Leu Leu Trp Gln Leu
            35                  40                  45

Asn Gly Arg Leu Glu Tyr Cys Leu Lys Asp Arg Met Asn Phe Asp
        50                  55                  60

Ile Pro Glu Glu Ile Lys Gln Leu Gln Gln Phe Gln Lys Glu Asp
    65                  70                  75

Ala Ala Leu Thr Ile Tyr Glu Met Leu Gln Asn Ile Phe Ala Ile
            80                  85                  90

Phe Arg Gln Asp Ser Ser Ser Thr Gly Trp Asn Glu Thr Ile Val
        95                  100                 105

Glu Asn Leu Leu Ala Asn Val Tyr His Gln Ile Asn His Leu Lys
    110                 115                 120

Thr Val Leu Glu Glu Lys Leu Glu Lys Glu Asp Phe Thr Arg Gly
```

```
                  125                 130                 135
Lys Leu Met Ser Ser Leu His Leu Lys Arg Tyr Tyr Gly Arg Ile
              140                 145                 150
Leu His Tyr Leu Lys Ala Lys Glu Tyr Ser His Cys Ala Trp Thr
              155                 160                 165
Ile Val Arg Val Glu Ile Leu Arg Asn Phe Tyr Phe Ile Asn Arg
              170                 175                 180
Leu Thr Gly Tyr Leu Arg Asn
              185

<210> SEQ ID NO 10
<211> LENGTH: 276
<212> TYPE: DNA
<213> ORGANISM: Homo sapiens
<220> FEATURE:
<221> NAME/KEY: unsure
<222> LOCATION: 163
<223> OTHER INFORMATION: unknown base

<400> SEQUENCE: 10
aaactttctg cttcctcaga agtctttgag tcctcagcag taccaaaaag           50
gacacactct ggccattctc catgagatgc ttcagcagat cttcagcctc          100
ttcagggcaa atatttctct ggatggttgg gaggaaaacc acacggagaa          150
attcctcatt canttcatc aacagctaga atacctagaa gcactcatgg           200
gactggaagc agagaagcta agtggtactt tgggtagtga taaccttaga          250
ttacaagtta aatgtactt ccgaag                                     276

<210> SEQ ID NO 11
<211> LENGTH: 1502
<212> TYPE: DNA
<213> ORGANISM: Homo Sapiens

<400> SEQUENCE: 11
tttttttttt tttttttttt tttttttttg aagaatcaac catattaatg           50
aatttatttt gacatacaaa caatttaaaa tggatagaat atataaagcc          100
acattacaaa ataaaaacaa ttgtggtcaa tatgcacaat cttaaaactc          150
agataaatat atatatacac aaaatcaaag caatgtgatt gtactataaa          200
ttgtattacc actctatgaa gaatcatgtc tggagaagtc ctctagtccc          250
tccacctacc tcgggcttct aaactctgta gtaagctctt gcttcatgtc          300
gttcaagggt cttccttgtt tgctcagttt ttctgtgaga ctgaacacaa          350
agaacagaca tcggctgatt tctacttgga caatggccca ggcacaggtg          400
ctgtagtcct ggttttccag gtaatcatgg atccttcgga agtacatttt          450
aacttgtaat ctaaggttat cactacccaa agtaccactt agcttctctg          500
cttccagtcc catgagtgct tctaggtatt ctagctgttg atgaagttga          550
atgaggaatt tctccgtgtg gttttcctcc caaccatcca gagaaatatt          600
tgccctgaag aggctgaaga tctgctgaag catctcatgg agaatggcca          650
gagtgtgtcc ttttggtac tgctgaggac tcaaagactt ctgaggaagc           700
agaaagtttt tcctgtgtgg tagacactgc tgaattgaca aggtttgcaa          750
cttattcaag agttttaaac tttcttgatt cacttgtctt tgctggaaga          800
```

-continued

```
taatcagttt caaatctaga gagaagatag tggtagaggc cagcagcacc         850
aacacagttc caaagaagtg cttgataatc atggtgaagg tcaaatatgc         900
tacttatccc tgcatagact tagggaaatt ccagctctag tgaatgtttg         950
cctttcatgc atctcagatt attttggaga gtgttctctt ttgttgcttt        1000
cgttttctaa tgtcatttct ccaagtttac acattagatt ttcaggttcc        1050
cttttcatgg tgttcagagt acattttctc catttcccta ttgtgttggc        1100
tattttgagg aagtaccaaa ataacttatt cattgtatgc tttccttgag        1150
gcaattacag actagtcatc aacataatc ttttattatt ctattcatta         1200
tatacaaagt ttcactgaac acaatgtgct ttctaaatat ttagtcaagc        1250
ttattaaagt tcttttattg agattacatt tttttcagta atagtctttc        1300
atggagtaaa acttaaccaa aggcttatca gcacctataa agaattcagg        1350
ggcaaaactt aaaataccta caaactacta aatttaaaac ctcaattaga        1400
actgtaaatt gtcacaaatg cttgagcaaa taattaattt taaaacatat        1450
atcagcaatc ttaaattatt ttatatctta tcctatcagt ttaatatcta        1500
ag                                                            1502
```

<210> SEQ ID NO 12
<211> LENGTH: 91
<212> TYPE: PRT
<213> ORGANISM: Homo sapiens
<220> FEATURE:
<221> NAME/KEY: unsure
<222> LOCATION: 54
<223> OTHER INFORMATION: unknown amino acid

<400> SEQUENCE: 12

```
Asn Phe Leu Leu Pro Gln Lys Ser Leu Ser Pro Gln Gln Tyr Gln
 1               5                  10                  15

Lys Gly His Thr Leu Ala Ile Leu His Glu Met Leu Gln Gln Ile
                20                  25                  30

Phe Ser Leu Phe Arg Ala Asn Ile Ser Leu Asp Gly Trp Glu Glu
                35                  40                  45

Asn His Thr Glu Lys Phe Leu Ile Xaa Leu His Gln Gln Leu Glu
                50                  55                  60

Tyr Leu Glu Ala Leu Met Gly Leu Glu Ala Glu Lys Leu Ser Gly
                65                  70                  75

Thr Leu Gly Ser Asp Asn Leu Arg Leu Gln Val Lys Met Tyr Phe
                80                  85                  90

Arg
```

What is claimed is:

1. An isolated nucleic acid comprising DNA having at least about 80% sequence identity to (a) a DNA molecule encoding a human interferon-ε polypeptide comprising the sequence of amino acids from about 22 to 189 of FIG. 1 (SEQ ID NO:1), or (b) the complement of the DNA molecule of (a), wherein said polypeptide has the ability to activate the JAK-STAT signaling pathway.

2. The isolated nucleic acid of claim 1 comprising DNA having at least about 80% sequence identity to (a) a DNA molecule encoding an IFN-ε polypeptide comprising the sequence of amino acids from about 22 to 208 of FIG. 1 (SEQ ID NO: 1), or (b) the complement of the DNA molecule of (a).

3. The isolated nucleic acid of claim 1 comprising DNA having at least about 80% sequence identity to (a) a DNA molecule encoding an IFN-ε polypeptide comprising the sequence of amino acids from about 1 to 208 of FIG. 1 (SEQ ID NO:1), or the complement of the DNA molecule of (a).

4. An isolated nucleic acid comprising DNA having at least about 80% sequence identity to (a) a DNA molecule encoding the same mature polypeptide encoded by the human interferon cDNA in ATCC Deposit No. 209509 (DNA50960-1224), or (b) the complement of the DNA molecule of (a), wherein said polypeptide has the ability to activate the JAK-STAT signaling pathway.

5. An isolated nucleic acid molecule encoding an IFN-ε polypeptide comprising DNA that hybridizes under conditions of 1) 0.015 M sodium chloride/0.0015 M sodium citrate/0.1% sodium dodecyl sulfate at 50° C. for washing, 2) 50% v/v formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C. during hybridization, or 3) 50% formamide, 5×SSC, (0.75 M sodium chloride, 0.075 M sodium citrate), 50 mM sodium phosphate (pH 6.8), 0.1% sodium pyrophosphate, 5×Denhardt's solution, sonicated salmon sperm DNA (50 μg/ml)) 0.1% SDS, and 10% dextran sulfate at 42° C., with washes at 42° C. in 0.2×SSC (sodium chloride/sodium citrate) and 50% formamide at 55° C., followed by a wash consisting of 0.1×SSC containing EDTA at 55° C. to the complement of a DNA molecule that encodes amino acids 22 to 189 of FIG. 1 (SEQ ID NO:1).

6. A vector comprising the nucleic acid of claim 1 or claim 5.

7. The vector of claim 6 operably linked to control sequences recognized by a host cell transformed with the vector.

8. A host cell comprising the vector of claim 6.

9. The host cell of claim 8 wherein said cell is a CHO cell.

10. The host cell of claim 8 wherein said cell is an *E coli*.

11. The host cell of claim 8 wherein said cell is a yeast cell.

12. A process for producing an IFN-ε polypeptide comprising culturing the host cell of claim 8 under conditions suitable for expression of IFN-ε and recovering IFN-ε from the cell culture.

13. The isolated nucleic acid molecule of claim 5, wherein said DNA molecule comprises the nucleotide sequence depicted in FIG. 2 (SEQ ID NO:2).

14. An isolated polypeptide comprising a sequence having at least about 80% amino acid sequence identity with the sequence of amino acids from about 22 to 189 of FIG. 1 (SEQ ID NO:1), wherein said polypeptide has the ability to activate the JAK-STAT signaling pathway.

15. An isolated IFN-ε polypeptide comprising a polypeptide encoded by a nucleic acid molecule hybridizing under conditions of 1) 0.015 M sodium chloride/0.0015 M sodium citrate/0.1% sodium dodecyl sulfate at 50° C. for washing, 2) 50% v/v formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C. during hybridization, or 3) 50% formamide, 5×SSC, (0.75 M sodium chloride, 0.075 M sodium citrate), 50 mM sodium phosphate (pH 6.8), 0.1% sodium pyrophosphate, 5×Denhardt's solution, sonicated salmon sperm DNA (50 μg/ml)) 0.1% SDS, and 10% dextran sulfate at 42° C., with washes at 42° C. in 0.2×SSC (sodium chloride/sodium citrate) and 50% formamide at 55° C., followed by a wash consisting of 0.1×SSC containing EDTA at 55° C. to the complement of a nucleic acid that encodes amino acids 22 to 189 of FIG. 1 (SEQ ID NO:1).

16. The IFN-ε polypeplide of claim 15, wherein said polypeptide comprises amino acid residues 22 to 208 of FIG. 1 (SEQ ID NO:1).

17. The polypeptide of claim 15 which is unglycosylated.

18. A chimeric molecule comprising the IFN-ε polypeptide of claim 15 fused to a heterologous amino acid sequence.

19. The chimeric molecule of claim 18 wherein said heterologous amino acid sequence is an epitope tag sequence.

20. The chimeric molecule of claim 18 wherein said heterologous amino acid sequence is a Fc region of an immunoglobulin.

21. A composition comprising the IFN-ε polypeptide of claim 15, in admixture with a pharmaceutically acceptable carrier.

22. A method for inhibiting the growth of a tumor cell comprising exposing the cell to an effective amount of the IFN-ε polypeptide of claim 15 wherein said polypeptide has tumor cell growth inhibitory activity and wherein said tumor cell bears a receptor for said IFN-ε polypeptide.

23. A method for treating a viral infection comprising administering a therapeutically effective amount of the IFN-ε polypeptide of claim 15 wherein said polypeptide has antiviral activity.

24. A method for upregulation of the immune system comprising administering a therapeutically effective amount of the IFN-ε polypeptide of claim 15 wherein said polypeptide has immunostimulatory activity.

25. An article of manufacture, comprising:
   a container; and
   a composition comprising an active ingredient contained within the container; wherein the composition is effective for inhibiting neoplastic cell growth and/or to cause apoptosis, and the active agent is the IFN-ε polypeptide of claim 15.

* * * * *